US009801398B2

(12) United States Patent
Olinski et al.

(10) Patent No.: US 9,801,398 B2
(45) Date of Patent: Oct. 31, 2017

(54) USE OF POLYPEPTIDES HAVING PROTEASE ACTIVITY IN ANIMAL FEED AND DETERGENTS

(71) Applicant: Novozymes A/S, Bagsvaerd (DK)

(72) Inventors: Robert Piotr Olinski, Vaerloese (DK); Tine Hoff, Holte (DK); Peter Rahbek Oestergaard, Virum (DK); Carsten Sjoeholm, Virum (DK); Katrine Pontoppidan, Lynge (DK)

(73) Assignee: Novozymes A/S, Bagsvaerd (DK)

( * ) Notice: Subject to any disclaimer, the term of this patent is extended or adjusted under 35 U.S.C. 154(b) by 175 days.

(21) Appl. No.: 14/372,590

(22) PCT Filed: Jan. 25, 2013

(86) PCT No.: PCT/EP2013/051448
§ 371 (c)(1),
(2) Date: Jul. 16, 2014

(87) PCT Pub. No.: WO2013/110766
PCT Pub. Date: Aug. 1, 2013

(65) Prior Publication Data
US 2014/0363538 A1 Dec. 11, 2014

Related U.S. Application Data

(60) Provisional application No. 61/590,998, filed on Jan. 26, 2012.

(30) Foreign Application Priority Data
Jan. 26, 2012 (EP) .................... 12152669

(51) Int. Cl.
A23K 20/174 (2016.01)
A23K 10/00 (2016.01)
A23K 1/16 (2006.01)
C12N 9/52 (2006.01)
A23J 1/18 (2006.01)
C11D 3/386 (2006.01)
C12N 9/60 (2006.01)
A23K 20/147 (2016.01)
A23K 20/142 (2016.01)
A23K 20/189 (2016.01)

(52) U.S. Cl.
CPC .............. A23K 1/1631 (2013.01); A23J 1/18 (2013.01); A23K 20/142 (2016.05); A23K 20/147 (2016.05); A23K 20/174 (2016.05); A23K 20/189 (2016.05); C11D 3/386 (2013.01); C11D 3/38627 (2013.01); C11D 3/38636 (2013.01); C11D 3/38645 (2013.01); C11D 3/38654 (2013.01); C12N 9/52 (2013.01); C12N 9/60 (2013.01); C12Y 304/21014 (2013.01); A23V 2002/00 (2013.01)

(58) Field of Classification Search
None
See application file for complete search history.

(56) References Cited

U.S. PATENT DOCUMENTS

| 2,653,899 | A | 9/1953 | Bunch et al. |
| 8,535,927 | B1 | 9/2013 | Jones et al. |
| 2008/0004186 | A1 | 1/2008 | Estell et al. |
| 2009/0111161 | A1 | 4/2009 | Jones et al. |
| 2010/0095987 | A1 | 4/2010 | Jones et al. |
| 2011/0081711 | A1 | 4/2011 | Jones et al. |

FOREIGN PATENT DOCUMENTS

| WO | 95/28850 | A1 | 11/1995 | |
| WO | 01/58275 | A2 | 8/2001 | |
| WO | 01/58276 | A2 | 8/2001 | |
| WO | 02/052948 | A2 | 7/2002 | |
| WO | 2004/034776 | A2 | 4/2004 | |
| WO | 2004/072221 | A2 | 8/2004 | |
| WO | 2004/072279 | A2 | 8/2004 | |
| WO | WO 2004/072279 | * | 8/2004 | ............... C12N 9/58 |
| WO | 2004/077960 | A1 | 9/2004 | |
| WO | 2004/111220 | A1 | 12/2004 | |
| WO | 2004/111223 | A1 | 12/2004 | |
| WO | 2005/035747 | A1 | 4/2005 | |
| WO | 2005/052146 | A2 | 6/2005 | |
| WO | 2005/052161 | A2 | 6/2005 | |
| WO | 2005/123911 | A2 | 12/2005 | |
| WO | 2008/002472 | A2 | 1/2008 | |
| WO | 2008/048392 | A1 | 4/2008 | |
| WO | 2008/153925 | A2 | 12/2008 | |
| WO | 2008/153934 | A2 | 12/2008 | |
| WO | 2009/058679 | A1 | 5/2009 | |
| WO | 2013/110766 | A1 | 8/2013 | |

OTHER PUBLICATIONS

Isaksen et al, (2011) Starch- and Protein-degrading Enzymes: Biochemistry, Enzymology and Characteristics Relevant to Animal Feed Use. In Enzymes in Farm Animal Nutrition, $2^{nd}$ Edition eds. Bedford & Partridge. p. 85-95.*
UniProt_201606 database Acc#A4FNQ0 from Oliynyk et al, Complete genome sequence of the erythromycin-producing bacterium Saccharopolyspora erythraea NRRL23338. Nat. Biotechnol. 25:447-453(2007). Alignment with SEQ ID No: 5.*
Csepregi et al., UniProt Accession No. H0K7C9 (2012).

(Continued)

Primary Examiner — Sheridan Swope
(74) Attorney, Agent, or Firm — Elias Lambiris

(57) ABSTRACT

The present invention relates to the use of isolated polypeptides having protease activity and isolated polynucleotides encoding the polypeptides in animal feed and detergents. The invention also relates to nucleic acid constructs, vectors, and host cells comprising the polynucleotides as well as methods of producing and using the polypeptides in e.g. animal feed and detergents.

14 Claims, 3 Drawing Sheets

(56) References Cited

OTHER PUBLICATIONS

Jani et al., Bulletin of Environment, Pharmacology and Life Sciences, vol. 1, No. 6, pp. 84-92 (2012).
Jones et al., GeneSeq Accession No. AEA80317 (2005).
Jones et al., GeneSeq Accession No. AWA8820 (2005).
Klenk et al., UniProt Accession No. H8GAL4 (2012).
Lucas et al., UniProt Accession No. G4IXC2 (2011).
Lucas et al., UniProt Accession No. G4J6Q2 (2011).
Lucas et al., UniProt Accession No. H5XEH4 (2012).
Lucas et al., UniProt Accession No. I0V8H8 (2012).
Olinski et al., GeneSeq Accession No. BAR72286 (2013).
Oliynyk et al., UniProt Accession No. A4F726 (2007).
Pati et al., UniProt Accession No. C7MV18 (2009).
Strobel et al., UniProt Accession No. KOJQQ4 (2012).
Strobel et al., UniProt Accession No. KOJWC2 (2012).
Yum et al., UniProt Accession No. Q55353 (1996).
Lucas et al., UniProt Accession No. H1JPF3 (2012).
Pati et al., GenBank Accession No. CP001683 (2014).
Lucas et al, UniProt Accession No. D2PRB9 (2010).
Oliynyk et al., GenBank Accession No. AM420293 (2007).
Oliynyk et al., UniProt Accession No. A4FNQO (2007).
Oliynyk et al., Nature Biotechnology, vol. 25, pp. 447-453 (2007).
Pati et al., Standards in Genom Sciences, vol. 1, pp. 141-149 (2009).
Pati et al., EMBL Accession No. ACU96970 (2011).
Yum et al, Biosci. Biotech. Biochem., vol. 58, No. 3, pp. 470-474 (1994).
Strobel et al., BMC Genomics, vol. 13, No. 465, pp. 1-13 (2012).
Fang (ED), Daily Chemical Industry Technology, p. 65 (2008), English translation only SLS.
Shuwen et al., Shandong Fisheries, p. 311 (2003), English translation only SLS.
Oliynky et al., EBI Accession No. CAM05675 (2007).

* cited by examiner

SEQUENCE LISTING

```
<160> NUMBER OF SEQ ID NOS: 13

<210> SEQ ID NO 1
<211> LENGTH: 1122
<212> TYPE: DNA
<213> ORGANISM: Saccharopolyspora erythraea
<220> FEATURE:
<221> NAME/KEY: CDS
<222> LOCATION: (1)..(1122)
<220> FEATURE:
<221> NAME/KEY: sig_peptide
<222> LOCATION: (1)..(84)
<220> FEATURE:
<221> NAME/KEY: mat_peptide
<222> LOCATION: (553)..(1122)

<400> SEQUENCE: 1 atg aag cga aca att cgg ctg gcc ggt gtg gcc gtg ctc gcg gcg        45
Met Lys Arg Thr Ile Arg Leu Ala Gly Val Ala Val Leu Ala Ala
            -180                -175                -170 ggc acc atc gcc gcg atc ggc gca cca acc gtc ggc gcc gag ccg        90
Gly Thr Ile Ala Ala Ile Gly Ala Pro Thr Val Gly Ala Glu Pro
            -165                -160                -155 gtg tcg ccc gac ctc gtc gcg gcg atg gag cgc gac ctc ggc atc       135
Val Ser Pro Asp Leu Val Ala Ala Met Glu Arg Asp Leu Gly Ile
            -150                -145                -140 tcc gcc cag cag gcg cac gcg cgg ctg gcg cag gag gcc acg gcg       180
```

```
              Ser Ala Gln Gln Ala   His Ala Arg Leu Ala   Gln Glu Ala Thr Ala
                          -135                  -130                  -125 atg cgg gcc gac gcc   gag ctg agc cgc tcg   ctg ggc gag agc ttc               225
Met Arg Ala Asp Ala   Glu Leu Ser Arg Ser   Leu Gly Glu Ser Phe
            -120                  -115                  -110 ggc ggt tcc tac ttc   gac gcg gcg cgc ggc   aag ctc gtc gtc ggg gtg           273
Gly Gly Ser Tyr Phe   Asp Ala Ala Arg Gly   Lys Leu Val Val Gly Val
            -105                  -100                       -95 acc gag cag gcc gat   gcg gcg aag gtg cgg   gcg gcg gga gcc gag gcc           321
Thr Glu Gln Ala Asp   Ala Ala Lys Val Arg   Ala Ala Gly Ala Glu Ala
             -90                   -85                       -80 gcg gtc gtg ccg aac   agc ctg cgc gaa ctg   gac gcc acc aag gcg gcg           369
Ala Val Val Pro Asn   Ser Leu Arg Glu Leu   Asp Ala Thr Lys Ala Ala
             -75                   -70                       -65 ctg gac gcg atg gac   gct gcg gcg ccc gcc   tcg gtg acc ggc tgg tac           417
Leu Asp Ala Met Asp   Ala Ala Ala Pro Ala   Ser Val Thr Gly Trp Tyr
             -60                   -55                       -50 gtc gac gtg ccc agc   agc agc gtg gtc gtc   tcc gtc aac ggg cgc gac           465
Val Asp Val Pro Ser   Ser Ser Val Val Val   Ser Val Asn Gly Arg Asp
-45                               -40                       -30 gcc gcg acc gac gcc   ttc ctg gac aag gcg   aag gcc gcc ggt gac tcg           513
Ala Ala Thr Asp Ala   Phe Leu Asp Lys Ala   Lys Ala Ala Gly Asp Ser
             -25                   -20                       -15 gtg cgc gtg cag gag   gtc gcc gag tcg ccg   cgc ccg ctc tac aac gtg           561
Val Arg Val Gln Glu   Val Ala Glu Ser Pro   Arg Pro Leu Tyr Asn Val
             -10                    -5                    -1   1 gtc ggc ggc gac gcc   tac tac atg ggc gga   cgc tgc tcg gtg ggc ttc           609
Val Gly Gly Asp Ala   Tyr Tyr Met Gly Gly   Arg Cys Ser Val Gly Phe
  5                                 10                        15 tcg gtg cgc tcg tcc   tcc ggc cag gcg ggc   ttc gtc acc gcc ggg cac           657
Ser Val Arg Ser Ser   Ser Gly Gln Ala Gly   Phe Val Thr Ala Gly His
 20                                 25                        35 tgc ggt acc cgc ggc   acg gcg gtc tcc ggc   tac aac cag gtc gcc atg           705
Cys Gly Thr Arg Gly   Thr Ala Val Ser Gly   Tyr Asn Gln Val Ala Met
                40                  45                      50 ggc tcg ttc cag ggt   tcg tcc ttc ccg aac   aac gac tac gcc tgg gtc           753
Gly Ser Phe Gln Gly   Ser Ser Phe Pro Asn   Asn Asp Tyr Ala Trp Val
             55                    60                       65 tcg gtg aac tcg aac   tgg acg ccg cag ccg   tgg gtg aac ctc tac aac           801
Ser Val Asn Ser Asn   Trp Thr Pro Gln Pro   Trp Val Asn Leu Tyr Asn
             70                    75                       80 ggc tcg gcc cgc gtg   gtg tcg ggc tcg tcg   gcg gcg ccg gtg ggc agc           849
Gly Ser Ala Arg Val   Val Ser Gly Ser Ser   Ala Ala Pro Val Gly Ser
 85                                 90                       95 tcg atc tgc cgt tcc   ggt tcc acg acc ggc   tgg cac tgc ggc agc gtg           897
Ser Ile Cys Arg Ser   Gly Ser Thr Thr Gly   Trp His Cys Gly Ser Val
100                               105                    110                115 cag gcg ctg aac cag   acc gtc cgc tac gcg   gaa ggc acg gtc tac ggc           945
Gln Ala Leu Asn Gln   Thr Val Arg Tyr Ala   Glu Gly Thr Val Tyr Gly
                120                  125                     130 ctg acc cgc acc aac   gtc tgc gcc gag ccg   ggt gac tcc ggt ggc tcc           993
Leu Thr Arg Thr Asn   Val Cys Ala Glu Pro   Gly Asp Ser Gly Gly Ser
            135                    140                     145 ttc atc agc ggc aac   cag gcc cag ggc atg   acc tcg ggc ggc tcg ggc          1041
Phe Ile Ser Gly Asn   Gln Ala Gln Gly Met   Thr Ser Gly Gly Ser Gly
            150                    155                     160 aac tgc agc tcg ggc   ggc acg acc tac ttc   cag ccc gtc aac gag gcg          1089
Asn Cys Ser Ser Gly   Gly Thr Thr Tyr Phe   Gln Pro Val Asn Glu Ala
      165                          170                     175
```

```
ctg agc gcc tac ggc ctg agc ctg gtc agg ggt                    1122
Leu Ser Ala Tyr Gly Leu Ser Leu Val Arg Gly
180             185                 190

<210> SEQ ID NO 2
<211> LENGTH: 374
<212> TYPE: PRT
<213> ORGANISM: Saccharopolyspora erythraea

<400> SEQUENCE: 2

Met Lys Arg Thr Ile  Arg Leu Ala Gly Val  Ala Val Leu Ala Ala
                -180              -175               -170

Gly Thr Ile Ala Ala  Ile Gly Ala Pro Thr  Val Gly Ala Glu Pro
                -165              -160               -155

Val Ser Pro Asp Leu  Val Ala Ala Met Glu  Arg Asp Leu Gly Ile
                -150              -145               -140

Ser Ala Gln Gln Ala  His Ala Arg Leu Ala  Gln Glu Ala Thr Ala
                -135              -130               -125

Met Arg Ala Asp Ala  Glu Leu Ser Arg Ser  Leu Gly Glu Ser Phe
                -120              -115               -110

Gly Gly Ser Tyr Phe  Asp Ala Ala Arg Gly  Lys Leu Val Val Gly Val
                -105              -100                -95

Thr Glu Gln Ala Asp  Ala Ala Lys Val Arg  Ala Ala Gly Ala Glu Ala
                 -90               -85                -80

Ala Val Val Pro Asn  Ser Leu Arg Glu Leu  Asp Ala Thr Lys Ala Ala
                 -75               -70                -65

Leu Asp Ala Met Asp  Ala Ala Ala Pro Ala  Ser Val Thr Gly Trp Tyr
                 -60               -55                -50

Val Asp Val Pro Ser  Ser Ser Val Val Ser  Val Asn Gly Arg Asp
-45                   -40                -35                -30

Ala Ala Thr Asp Ala  Phe Leu Asp Lys Ala  Lys Ala Gly Asp Ser
                 -25               -20                -15

Val Arg Val Gln Glu  Val Ala Glu Ser Pro  Arg Pro Leu Tyr Asn Val
                 -10                -5                -1   1

Val Gly Gly Asp Ala Tyr Tyr Met Gly Gly Arg Cys Ser Val Gly Phe
5                   10                  15

Ser Val Arg Ser Ser Ser Gly Gln Ala Gly Phe Val Thr Ala Gly His
20                  25                  30                  35

Cys Gly Thr Arg Gly Thr Ala Val Ser Gly Tyr Asn Gln Val Ala Met
                40                  45                  50

Gly Ser Phe Gln Gly Ser Ser Phe Pro Asn Asn Asp Tyr Ala Trp Val
                55                  60                  65

Ser Val Asn Ser Asn Trp Thr Pro Gln Pro Trp Val Asn Leu Tyr Asn
                70                  75                  80

Gly Ser Ala Arg Val Val Ser Gly Ser Ser Ala Ala Pro Val Gly Ser
                85                  90                  95

Ser Ile Cys Arg Ser Gly Ser Thr Thr Gly Trp His Cys Gly Ser Val
100                 105                 110                 115

Gln Ala Leu Asn Gln Thr Val Arg Tyr Ala Glu Gly Thr Val Tyr Gly
                120                 125                 130

Leu Thr Arg Thr Asn Val Cys Ala Glu Pro Gly Asp Ser Gly Gly Ser
                135                 140                 145

Phe Ile Ser Gly Asn Gln Ala Gln Gly Met Thr Ser Gly Gly Ser Gly
                150                 155                 160

Asn Cys Ser Ser Gly Gly Thr Thr Tyr Phe Gln Pro Val Asn Glu Ala
```

```
                    165                 170                 175
Leu Ser Ala Tyr Gly Leu Ser Leu Val Arg Gly
180                 185                 190

<210> SEQ ID NO 3
<211> LENGTH: 1119
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (1)..(1119)
<220> FEATURE:
<221> NAME/KEY: sig_peptide
<222> LOCATION: (1)..(81)
<220> FEATURE:
<221> NAME/KEY: mat_peptide
<222> LOCATION: (550)..(1119)

<400> SEQUENCE: 3 atg aag aaa ccg  ttg ggg aaa att  gtc gca agc acc  gca cta ctc           45
Met Lys Lys Pro  Leu Gly Lys Ile  Val Ala Ser Thr  Ala Leu Leu
         -180                -175                -170 att tct gtt gct  ttt agt tca tcg  atc gca tcg gct  gaa ccg gta           90
Ile Ser Val Ala  Phe Ser Ser Ser  Ile Ala Ser Ala  Glu Pro Val
         -165                -160                -155 tct cct gac ttg  gtt gct gcg atg  gag cgc gat ctt  gga atc tct          135
Ser Pro Asp Leu  Val Ala Ala Met  Glu Arg Asp Leu  Gly Ile Ser
         -150                -145                -140 gct cag caa gcg  cat gct cgc tta  gct cag gaa gca  act gct atg          180
Ala Gln Gln Ala  His Ala Arg Leu  Ala Gln Glu Ala  Thr Ala Met
         -135                -130                -125 cgt gcg gat gct  gaa ttg tct cgc  tca ttg gga gaa  tct ttt gga          225
Arg Ala Asp Ala  Glu Leu Ser Arg  Ser Leu Gly Glu  Ser Phe Gly
         -120                -115                -110 ggt tct tac ttc  gat gca gca cgc  ggt aaa ctt gtt  gta ggt gta aca      273
Gly Ser Tyr Phe  Asp Ala Ala Arg  Gly Lys Leu Val  Val Gly Val Thr
         -105                -100                 -95 gaa caa gca gac  gct gct aag gta  cgc gct gcg gga  gct gaa gcg gca      321
Glu Gln Ala Asp  Ala Ala Lys Val  Arg Ala Ala Gly  Ala Glu Ala Ala
          -90                 -85                 -80 gtt gtt cct aac  tct tta cgt gaa  ttg gat gct aca  aaa gca gca tta      369
Val Val Pro Asn  Ser Leu Arg Glu  Leu Asp Ala Thr  Lys Ala Ala Leu
          -75                 -70                 -65 gat gca atg gac  gca gca gct cct  gcg agc gtt act  gga tgg tat gtt      417
Asp Ala Met Asp  Ala Ala Ala Pro  Ala Ser Val Thr  Gly Trp Tyr Val
 -60                 -55                 -50                 -45 gat gta cca tca  tct tca gta gtt  gta tct gta aat  ggt cgc gat gca      465
Asp Val Pro Ser  Ser Ser Val Val  Val Ser Val Asn  Gly Arg Asp Ala
                  -40                 -35                 -30 gca aca gat gcg  ttc ctt gac aaa  gct aag gct gct  gga gac tca gtt      513
Ala Thr Asp Ala  Phe Leu Asp Lys  Ala Lys Ala Ala  Gly Asp Ser Val
          -25                 -20                 -15 cgc gta caa gaa  gtt gcg gaa tca  ccg cgt cca ttg  tac aat gtt gta      561
Arg Val Gln Glu  Val Ala Glu Ser  Pro Arg Pro Leu  Tyr Asn Val Val
          -10                  -5                  -1   1 ggt ggc gat gcg  tac tat atg gga  gga cgc tgt tca  gtt ggt ttc tca      609
Gly Gly Asp Ala  Tyr Tyr Met Gly  Gly Arg Cys Ser  Val Gly Phe Ser
  5                  10                  15                  20 gtt cgc tct agc  tct ggc caa gct  ggt ttc gta aca  gct ggt cat tgc      657
Val Arg Ser Ser  Ser Gly Gln Ala  Gly Phe Val Thr  Ala Gly His Cys
                  25                  30                  35
```

-continued

```
ggt act cgc gga aca gct gtt tct ggt tac aat cag gta gct atg ggt      705
Gly Thr Arg Gly Thr Ala Val Ser Gly Tyr Asn Gln Val Ala Met Gly
        40                  45                  50 tca ttt caa gga tct tct ttt ccg aac aac gat tat gca tgg gta tct      753
Ser Phe Gln Gly Ser Ser Phe Pro Asn Asn Asp Tyr Ala Trp Val Ser
55                  60                  65 gtt aac tca aac tgg aca cct caa cca tgg gta aac ttg tac aat gga      801
Val Asn Ser Asn Trp Thr Pro Gln Pro Trp Val Asn Leu Tyr Asn Gly
        70                  75                  80 agc gct cgt gta gtt agc gga tca tca gct gca cca gtt ggt tct tca      849
Ser Ala Arg Val Val Ser Gly Ser Ser Ala Ala Pro Val Gly Ser Ser
85                  90                  95                 100 att tgc cgc tca gga tct aca act ggt tgg cat tgc ggc tct gtt cag      897
Ile Cys Arg Ser Gly Ser Thr Thr Gly Trp His Cys Gly Ser Val Gln
            105                 110                 115 gca ctt aac caa act gta cgt tac gct gag ggt act gtt tac ggc ttg      945
Ala Leu Asn Gln Thr Val Arg Tyr Ala Glu Gly Thr Val Tyr Gly Leu
        120                 125                 130 act cgt act aac gtt tgt gcg gaa cct ggc gat tct gga ggc tct ttc      993
Thr Arg Thr Asn Val Cys Ala Glu Pro Gly Asp Ser Gly Gly Ser Phe
    135                 140                 145 att tct ggt aac cag gca caa ggc atg acg agc ggt gga tct gga aat     1041
Ile Ser Gly Asn Gln Ala Gln Gly Met Thr Ser Gly Gly Ser Gly Asn
150                 155                 160 tgt tct tct gga ggt act acg tac ttt cag cca gtt aac gag gcg ttg     1089
Cys Ser Ser Gly Gly Thr Thr Tyr Phe Gln Pro Val Asn Glu Ala Leu
165                 170                 175                 180 agc gct tac gga ctt agc tta gtt cgt gga                             1119
Ser Ala Tyr Gly Leu Ser Leu Val Arg Gly
                185                 190

<210> SEQ ID NO 4
<211> LENGTH: 373
<212> TYPE: PRT
<213> ORGANISM: Artificial Sequence
<220> FEATURE:
<223> OTHER INFORMATION: Synthetic Construct

<400> SEQUENCE: 4

Met Lys Lys Pro Leu Gly Lys Ile Val Ala Ser Thr Ala Leu Leu
        -180                -175                -170

Ile Ser Val Ala Phe Ser Ser Ser Ile Ala Ser Ala Glu Pro Val
        -165                -160                -155

Ser Pro Asp Leu Val Ala Ala Met Glu Arg Asp Leu Gly Ile Ser
        -150                -145                -140

Ala Gln Gln Ala His Ala Arg Leu Ala Gln Glu Ala Thr Ala Met
        -135                -130                -125

Arg Ala Asp Ala Glu Leu Ser Arg Ser Leu Gly Glu Ser Phe Gly
        -120                -115                -110

Gly Ser Tyr Phe Asp Ala Ala Arg Gly Lys Leu Val Val Gly Val Thr
        -105                -100                -95

Glu Gln Ala Asp Ala Ala Lys Val Arg Ala Gly Ala Glu Ala Ala
    -90                 -85                 -80

Val Val Pro Asn Ser Leu Arg Glu Leu Asp Ala Thr Lys Ala Ala Leu
    -75                 -70                 -65

Asp Ala Met Asp Ala Ala Ala Pro Ala Ser Val Thr Gly Trp Tyr Val
-60                 -55                 -50                 -45

Asp Val Pro Ser Ser Ser Val Val Val Ser Val Asn Gly Arg Asp Ala
```

```
              -40                 -35                 -30
Ala Thr Asp Ala Phe Leu Asp Lys Ala Lys Ala Gly Asp Ser Val
            -25                 -20                 -15

Arg Val Gln Glu Val Ala Glu Ser Pro Arg Pro Leu Tyr Asn Val Val
            -10                  -5                  -1   1

Gly Gly Asp Ala Tyr Tyr Met Gly Gly Arg Cys Ser Val Gly Phe Ser
 5                   10                  15                  20

Val Arg Ser Ser Ser Gly Gln Ala Gly Phe Val Thr Ala Gly His Cys
                 25                  30                  35

Gly Thr Arg Gly Thr Ala Val Ser Gly Tyr Asn Gln Val Ala Met Gly
             40                  45                  50

Ser Phe Gln Gly Ser Ser Phe Pro Asn Asn Asp Tyr Ala Trp Val Ser
         55                  60                  65

Val Asn Ser Asn Trp Thr Pro Gln Pro Trp Val Asn Leu Tyr Asn Gly
         70                  75                  80

Ser Ala Arg Val Val Ser Gly Ser Ser Ala Ala Pro Val Gly Ser Ser
 85                  90                  95                 100

Ile Cys Arg Ser Gly Ser Thr Thr Gly Trp His Cys Gly Ser Val Gln
            105                 110                 115

Ala Leu Asn Gln Thr Val Arg Tyr Ala Glu Gly Thr Val Tyr Gly Leu
            120                 125                 130

Thr Arg Thr Asn Val Cys Ala Glu Pro Gly Asp Ser Gly Gly Ser Phe
            135                 140                 145

Ile Ser Gly Asn Gln Ala Gln Gly Met Thr Ser Gly Gly Ser Gly Asn
            150                 155                 160

Cys Ser Ser Gly Gly Thr Thr Tyr Phe Gln Pro Val Asn Glu Ala Leu
165                 170                 175                 180

Ser Ala Tyr Gly Leu Ser Leu Val Arg Gly
                185                 190

<210> SEQ ID NO 5
<211> LENGTH: 190
<212> TYPE: PRT
<213> ORGANISM: Saccharopolyspora erythraea
<220> FEATURE:
<221> NAME/KEY: mat_peptide
<222> LOCATION: (1)..(190)

<400> SEQUENCE: 5

Tyr Asn Val Val Gly Gly Asp Ala Tyr Tyr Met Gly Gly Arg Cys Ser
 1               5                  10                  15

Val Gly Phe Ser Val Arg Ser Ser Ser Gly Gln Ala Gly Phe Val Thr
             20                  25                  30

Ala Gly His Cys Gly Thr Arg Gly Thr Ala Val Ser Gly Tyr Asn Gln
         35                  40                  45

Val Ala Met Gly Ser Phe Gln Gly Ser Ser Phe Pro Asn Asn Asp Tyr
 50                  55                  60

Ala Trp Val Ser Val Asn Ser Asn Trp Thr Pro Gln Pro Trp Val Asn
65                  70                  75                  80

Leu Tyr Asn Gly Ser Ala Arg Val Val Ser Gly Ser Ser Ala Ala Pro
             85                  90                  95

Val Gly Ser Ser Ile Cys Arg Ser Gly Ser Thr Thr Gly Trp His Cys
            100                 105                 110

Gly Ser Val Gln Ala Leu Asn Gln Thr Val Arg Tyr Ala Glu Gly Thr
            115                 120                 125
```

```
Val Tyr Gly Leu Thr Arg Thr Asn Val Cys Ala Glu Pro Gly Asp Ser
        130                 135                 140

Gly Gly Ser Phe Ile Ser Gly Asn Gln Ala Gln Gly Met Thr Ser Gly
145                 150                 155                 160

Gly Ser Gly Asn Cys Ser Ser Gly Gly Thr Thr Tyr Phe Gln Pro Val
            165                 170                 175

Asn Glu Ala Leu Ser Ala Tyr Gly Leu Ser Leu Val Arg Gly
        180                 185                 190

<210> SEQ ID NO 6
<211> LENGTH: 27
<212> TYPE: PRT
<213> ORGANISM: Artificial Sequence
<220> FEATURE:
<223> OTHER INFORMATION: Bacillus lentus secretion signal
<220> FEATURE:
<221> NAME/KEY: SIGNAL
<222> LOCATION: (1)..(27)

<400> SEQUENCE: 6

Met Lys Lys Pro Leu Gly Lys Ile Val Ala Ser Thr Ala Leu Leu Ile
1               5                   10                  15

Ser Val Ala Phe Ser Ser Ser Ile Ala Ser Ala
            20                  25

<210> SEQ ID NO 7
<211> LENGTH: 1596
<212> TYPE: DNA
<213> ORGANISM: Nocardiopsis sp. NRRL 18262
<220> FEATURE:
<221> NAME/KEY: CDS
<222> LOCATION: (318)..(1463)
<220> FEATURE:
<221> NAME/KEY: sig_peptide
<222> LOCATION: (318)..(404)
<220> FEATURE:
<221> NAME/KEY: mat_peptide
<222> LOCATION: (900)..(1463)

<400> SEQUENCE: 7
acgtttggta cgggtaccgg tgtccgcatg tggccagaat gccccccttgc gacagggaac      60 ggattcggtc ggtagcgcat cgactccgac aaccgcgagg tggccgttcg cgtcgccacg     120
ttctgcgacc gtcatgcgac ccatcatcgg gtgaccccac cgagctctga atggtccacc     180
gttctgacgg tctttccctc accaaaacgt gcacctatgg ttaggacgtt gtttaccgaa     240
tgtctcggtg aacgacaggg gccggacggt attcggcccc gatccccgt tgatccccc      300 aggagagtag ggacccc atg cga ccc tcc ccc gtt gtc tcc gcc atc ggt       350
                   Met Arg Pro Ser Pro Val Val Ser Ala Ile Gly
                        -190             -185 acg gga gcg ctg gcc ttc ggt ctg gcg ctg tcc ggt acc ccg ggt          395
Thr Gly Ala Leu Ala Phe Gly Leu Ala Leu Ser Gly Thr Pro Gly
        -180                -175                -170 gcc ctc gcg gcc acc gga gcg ctc ccc cag tca ccc acc ccg gag          440
Ala Leu Ala Ala Thr Gly Ala Leu Pro Gln Ser Pro Thr Pro Glu
        -165                -160                -155 gcc gac gcg gtc tcc atg cag gag gcg ctc cag cgc gac ctc gac          485
Ala Asp Ala Val Ser Met Gln Glu Ala Leu Gln Arg Asp Leu Asp
        -150                -145                -140 ctg acc tcc gcc gag gcc gag gag ctg ctg gcc gcc cag gac acc          530
Leu Thr Ser Ala Glu Ala Glu Glu Leu Leu Ala Ala Gln Asp Thr
        -135                -130                -125 gcc ttc gag gtc gac gag gcc gcg gcc gag gcc gcc ggg gac gcc          575
```

```
Ala Phe Glu Val  Asp Glu Ala Ala  Ala Glu Ala Ala  Gly Asp Ala
        -120              -115              -110 tac ggc ggc tcc  gtc ttc gac acc  gag agc ctg gaa  ctg acc gtc ctg      623
Tyr Gly Gly Ser  Val Phe Asp Thr  Glu Ser Leu Glu  Leu Thr Val Leu
        -105              -100               -95 gtc acc gat gcc  gcc gcg gtc gag  gcc gtg gag gcc  acc ggc gcc ggg      671
Val Thr Asp Ala  Ala Ala Val Glu  Ala Val Glu Ala  Thr Gly Ala Gly
         -90               -85               -80 acc gag ctg gtc  tcc tac ggc atc  gac ggt ctc gac  gag atc gtc cag      719
Thr Glu Leu Val  Ser Tyr Gly Ile  Asp Gly Leu Asp  Glu Ile Val Gln
         -75               -70               -65 gag ctc aac gcc  gcc gac gcc gtt  ccc ggt gtg gtc  ggc tgg tac ccg      767
Glu Leu Asn Ala  Ala Asp Ala Val  Pro Gly Val Val  Gly Trp Tyr Pro
-60                       -55               -50                -45 gac gtg gcg ggt  gac acc gtc gtc  ctg gag gtc ctg  gag ggt tcc gga      815
Asp Val Ala Gly  Asp Thr Val Val  Leu Glu Val Leu  Glu Gly Ser Gly
                  -40               -35                -30 gcc gac gtc agc  ggc ctg ctc gcg  gac gcc ggc gtg  gac gcc tcg gcc      863
Ala Asp Val Ser  Gly Leu Leu Ala  Asp Ala Gly Val  Asp Ala Ser Ala
             -25               -20                -15 gtc gag gtg acc  acg agc gac cag  ccc gag ctc tac  gcc gac atc atc      911
Val Glu Val Thr  Thr Ser Asp Gln  Pro Glu Leu Tyr  Ala Asp Ile Ile
         -10                -5               -1   1 ggt ggc ctg gcc  tac acc atg ggc  ggc cgc tgt tcg  gtc ggc ttc gcg      959
Gly Gly Leu Ala  Tyr Thr Met Gly  Gly Arg Cys Ser  Val Gly Phe Ala
5                         10               15                  20 gcc acc aac gcc  gcc ggt cag ccc  ggg ttc gtc acc  gcc ggt cac tgc      1007
Ala Thr Asn Ala  Ala Gly Gln Pro  Gly Phe Val Thr  Ala Gly His Cys
                 25                30                     35 ggc cgc gtg ggc  acc cag gtg acc  atc ggc aac ggc  agg ggc gtc ttc      1055
Gly Arg Val Gly  Thr Gln Val Thr  Ile Gly Asn Gly  Arg Gly Val Phe
             40                45                     50 gag cag tcc gtc  ttc ccc ggc aac  gac gcg gcc ttc  gtc cgc ggt acg      1103
Glu Gln Ser Val  Phe Pro Gly Asn  Asp Ala Ala Phe  Val Arg Gly Thr
        55                60                    65 tcc aac ttc acg  ctg acc aac ctg  gtc agc cgc tac  aac acc ggc ggg      1151
Ser Asn Phe Thr  Leu Thr Asn Leu  Val Ser Arg Tyr  Asn Thr Gly Gly
70                        75                80 tac gcc acg gtc  gcc ggt cac aac  cag gcc ccc atc  ggc tcc tcc gtc      1199
Tyr Ala Thr Val  Ala Gly His Asn  Gln Ala Pro Ile  Gly Ser Ser Val
85                         90                95                 100 tgc cgc tcc ggc  tcc acc acc ggt  tgg cac tgc ggc  acc atc cag gcc      1247
Cys Arg Ser Gly  Ser Thr Thr Gly  Trp His Cys Gly  Thr Ile Gln Ala
                 105                110                     115 cgc ggc cag tcg  gtg agc tac ccc  gag ggc acc gtc  acc aac atg acc      1295
Arg Gly Gln Ser  Val Ser Tyr Pro  Glu Gly Thr Val  Thr Asn Met Thr
             120                125                     130 cgg acc acc gtg  tgc gcc gag ccc  ggc gac tcc ggc  ggc tcc tac atc      1343
Arg Thr Thr Val  Cys Ala Glu Pro  Gly Asp Ser Gly  Gly Ser Tyr Ile
         135                140                     145 tcc ggc acc cag  gcc cag ggc gtg  acc tcc ggc ggc  tcc ggc aac tgc      1391
Ser Gly Thr Gln  Ala Gln Gly Val  Thr Ser Gly Gly  Ser Gly Asn Cys
         150                155                     160 cgc acc ggc ggg  acc acc ttc tac  cag gag gtc acc  ccc atg gtg aac      1439
Arg Thr Gly Gly  Thr Thr Phe Tyr  Gln Glu Val Thr  Pro Met Val Asn
165                       170                175                 180 tcc tgg ggc gtc  cgt ctc cgg acc  tgatccccgc ggttccaggc ggaccgacgg     1493
Ser Trp Gly Val  Arg Leu Arg Thr
                 185
```
tcgtgacctg agtaccaggc gtccccgccg cttccagcgg cgtccgcacc ggggtgggac    1553
cgggcgtggc cacggcccca cccgtgaccg gaccgcccgg cta    1596

<210> SEQ ID NO 8
<211> LENGTH: 382
<212> TYPE: PRT
<213> ORGANISM: Nocardiopsis sp. NRRL 18262

<400> SEQUENCE: 8

```
Met Arg Pro Ser Pro  Val Val Ser Ala Ile  Gly Thr Gly Ala Leu
                -190              -185              -180

Ala Phe Gly Leu Ala  Leu Ser Gly Thr Pro  Gly Ala Leu Ala Ala
                -175              -170              -165

Thr Gly Ala Leu Pro  Gln Ser Pro Thr Pro  Glu Ala Asp Ala Val
                -160              -155              -150

Ser Met Gln Glu Ala  Leu Gln Arg Asp Leu  Asp Leu Thr Ser Ala
                -145              -140              -135

Glu Ala Glu Glu Leu  Leu Ala Ala Gln Asp  Thr Ala Phe Glu Val
                -130              -125              -120

Asp Glu Ala Ala Ala  Glu Ala Ala Gly Asp  Ala Tyr Gly Gly Ser
                -115              -110              -105

Val Phe Asp Thr Glu  Ser Leu Glu Leu Thr  Val Leu Val Thr Asp Ala
                -100              -95               -90

Ala Ala Val Glu Ala  Val Gly Ala Thr Gly  Ala Gly Thr Glu Leu Val
        -85                   -80                   -75

Ser Tyr Gly Ile Asp  Gly Leu Asp Glu Ile  Val Gln Glu Leu Asn Ala
        -70                   -65                   -60

Ala Asp Ala Val Pro  Gly Val Val Gly Trp  Tyr Pro Asp Val Ala Gly
        -55                   -50                   -45

Asp Thr Val Val Leu  Glu Val Leu Glu Gly  Ser Gly Ala Asp Val Ser
-40                   -35                   -30                   -25

Gly Leu Leu Ala Asp  Ala Gly Val Asp Ala  Ser Ala Val Glu Val Thr
                -20                   -15                   -10

Thr Ser Asp Gln Pro  Glu Leu Tyr Ala Asp  Ile Ile Gly Gly Leu Ala
        -5                    -1  1                  5

Tyr Thr Met Gly Gly  Arg Cys Ser Val Gly  Phe Ala Ala Thr Asn Ala
        10                    15                    20

Ala Gly Gln Pro Gly  Phe Val Thr Ala Gly  His Cys Gly Arg Val Gly
25                    30                    35                    40

Thr Gln Val Thr Ile  Gly Asn Gly Arg Gly  Val Phe Glu Gln Ser Val
                45                    50                    55

Phe Pro Gly Asn Asp  Ala Ala Phe Val Arg  Gly Thr Ser Asn Phe Thr
                60                    65                    70

Leu Thr Asn Leu Val  Ser Arg Tyr Asn Thr  Gly Gly Tyr Ala Thr Val
        75                    80                    85

Ala Gly His Asn Gln  Ala Pro Ile Gly Ser  Ser Val Cys Arg Ser Gly
        90                    95                    100

Ser Thr Thr Gly Trp  His Cys Gly Thr Ile  Gln Ala Arg Gly Gln Ser
105                   110                   115                   120

Val Ser Tyr Pro Glu  Gly Thr Val Thr Asn  Met Thr Arg Thr Thr Val
                125                   130                   135

Cys Ala Glu Pro Gly  Asp Ser Gly Gly Ser  Tyr Ile Ser Gly Thr Gln
                140                   145                   150

Ala Gln Gly Val Thr  Ser Gly Gly Ser Gly  Asn Cys Arg Thr Gly Gly
```

155                 160                 165
Thr Thr Phe Tyr Gln Glu Val Thr Pro Met Val Asn Ser Trp Gly Val
        170                 175                 180

Arg Leu Arg Thr
185

<210> SEQ ID NO 9
<211> LENGTH: 381
<212> TYPE: PRT
<213> ORGANISM: Saccharomonospora viridis

<400> SEQUENCE: 9

Met Leu Pro Lys Lys His Arg Leu Val Ala Arg Met Thr Ala Thr Ala
1               5                   10                  15

Met Leu Ala Ala Gly Thr Ala Ala Val Ala Leu Pro Ala Thr Ala
            20                  25                  30

Glu Thr Val Thr Pro Gln Thr Glu Val Thr Ala Glu Ala Asp Pro Met
            35                  40                  45

Leu Gln Ala Met Gln Arg Asp Leu Gly Leu Thr Ala Gln Glu Ala Gln
    50                  55                  60

Gln Arg Leu Glu Gln Glu Ser Val Ala Arg Thr Leu Asp Glu Thr Leu
65                  70                  75                  80

Arg Ala Lys Leu Gln Asp Asn Phe Gly Gly Ser Tyr Tyr Asp Ala Asp
                85                  90                  95

Thr Gly Thr Leu Val Val Gly Val Thr Glu Ala Ser Ala Leu Asp Asp
            100                 105                 110

Val Arg Ala Ala Gly Ala Lys Ala Lys Leu Val Asp Ala Ser Ile Asp
        115                 120                 125

Glu Leu Asn Thr Ala Val Asp Arg Leu Asp Arg Lys Glu Ser Ser Ala
    130                 135                 140

Pro Glu Ser Val Thr Gly Trp Tyr Val Asp Val Lys Asn Asn Ser Val
145                 150                 155                 160

Val Val Thr Thr Ala Pro Gly Thr Ala Ala Gln Ala Glu Lys Phe Val
                165                 170                 175

Ala Ala Ser Gly Val Asp Gly Asp Asn Val Glu Ile Val Glu Ser Thr
            180                 185                 190

Glu Gln Pro Arg Thr Phe Met Asp Val Ile Gly Gly Asn Ala Tyr Tyr
        195                 200                 205

Met Gly Asn Gly Gly Arg Cys Ser Val Gly Phe Thr Val Gln Gly Gly
    210                 215                 220

Phe Val Thr Ala Gly His Cys Gly Thr Thr Gly Thr Ser Thr Ser Ser
225                 230                 235                 240

Pro Ser Gly Thr Phe Ala Gly Ser Ser Phe Pro Gly Asn Asp Tyr Ala
                245                 250                 255

Phe Val Arg Thr Gly Ser Gly Asp Thr Leu Arg Pro Trp Val Asn Met
            260                 265                 270

Tyr Asn Gly Ser Ala Arg Val Val Ser Gly Ser Ser Val Ala Pro Val
        275                 280                 285

Gly Ser Ser Ile Cys Arg Ser Gly Ser Thr Thr Gly Trp His Cys Gly
    290                 295                 300

Gln Val Gln Ala Phe Asn Gln Thr Val Arg Tyr Ala Glu Gly Thr Val
305                 310                 315                 320

Thr Gly Leu Thr Arg Thr Asn Val Cys Ala Glu Pro Gly Asp Ser Gly
                325                 330                 335

```
Gly Ser Phe Ile Ser Gly Asn Gln Ala Gln Gly Met Thr Ser Gly Gly
                340                 345                 350

Ser Gly Asn Cys Thr Phe Gly Thr Thr Tyr Phe Gln Pro Val Asn
        355                 360                 365

Glu Val Leu Ser Ala Tyr Asn Leu Arg Leu Ile Thr Gly
        370                 375                 380

<210> SEQ ID NO 10
<211> LENGTH: 382
<212> TYPE: PRT
<213> ORGANISM: Streptomyces sp.

<400> SEQUENCE: 10

Met Arg His Thr Gly Arg Asn Ala Ile Gly Ala Ala Ile Ala Ala Ser
1               5                   10                  15

Ala Leu Ala Phe Ala Leu Val Pro Ser Gln Ala Ala Ala Asn Asp Thr
                20                  25                  30

Leu Thr Glu Arg Ala Glu Ala Val Ala Asp Leu Pro Ala Gly Val
            35                  40                  45

Leu Asp Ala Met Glu Arg Asp Leu Gly Leu Ser Glu Gln Glu Ala Gly
50                  55                  60

Leu Lys Leu Val Ala Glu His Asp Ala Ala Leu Leu Gly Glu Thr Leu
65                  70                  75                  80

Ser Ala Asp Leu Asp Ala Phe Ala Gly Ser Trp Leu Ala Glu Gly Thr
                85                  90                  95

Glu Leu Val Val Ala Thr Thr Ser Glu Ala Glu Ala Ala Glu Ile Thr
            100                 105                 110

Glu Ala Gly Ala Thr Ala Glu Val Val Asp His Thr Leu Ala Glu Leu
        115                 120                 125

Asp Ser Val Lys Asp Ala Leu Asp Thr Ala Ala Glu Ser Tyr Asp Thr
    130                 135                 140

Thr Asp Ala Pro Val Trp Tyr Val Asp Val Thr Thr Asn Gly Val Val
145                 150                 155                 160

Leu Leu Thr Ser Asp Val Thr Glu Ala Glu Gly Phe Val Glu Ala Ala
                165                 170                 175

Gly Val Asn Ala Ala Ala Val Asp Ile Gln Thr Ser Asp Glu Gln Pro
            180                 185                 190

Gln Ala Phe Tyr Asp Leu Val Gly Gly Asp Ala Tyr Tyr Met Gly Gly
        195                 200                 205

Gly Arg Cys Ser Val Gly Phe Ser Val Thr Gln Gly Ser Thr Pro Gly
    210                 215                 220

Phe Ala Thr Ala Gly His Cys Gly Thr Val Gly Thr Ser Thr Thr Gly
225                 230                 235                 240

Tyr Asn Gln Ala Gln Gly Thr Phe Glu Glu Ser Ser Phe Pro Gly
                245                 250                 255

Asp Asp Met Ala Trp Val Ser Val Asn Ser Asp Trp Asn Thr Thr Pro
            260                 265                 270

Thr Val Asn Glu Gly Glu Val Thr Val Ser Gly Ser Thr Glu Ala Ala
        275                 280                 285

Val Gly Ala Ser Ile Cys Arg Ser Gly Ser Thr Thr Gly Trp His Cys
    290                 295                 300

Gly Thr Ile Gln Gln His Asn Thr Ser Val Thr Tyr Pro Glu Gly Thr
305                 310                 315                 320

Ile Thr Gly Val Thr Arg Thr Ser Val Cys Ala Glu Pro Gly Asp Ser
                325                 330                 335
```

```
Gly Gly Ser Tyr Ile Ser Gly Ser Gln Ala Gln Gly Val Thr Ser Gly
            340                 345                 350

Gly Ser Gly Asn Cys Thr Ser Gly Thr Thr Tyr His Gln Pro Ile
            355                 360                 365

Asn Pro Leu Leu Ser Ala Tyr Gly Leu Asp Leu Val Thr Gly
            370                 375                 380

<210> SEQ ID NO 11
<211> LENGTH: 378
<212> TYPE: PRT
<213> ORGANISM: Saccharomonospora xinjiangensis

<400> SEQUENCE: 11

Met Asn Arg Lys Asn Ala Ala Arg Leu Ile Ala Ser Val Thr Leu Ala
1               5                   10                  15

Ala Gly Thr Ala Val Ala Phe Thr Leu Pro Ala Thr Ala Ala Pro Ala
            20                  25                  30

Ala Asp Ala Val Val Pro Ala Thr Ala Ala Asp Pro Val Val Gln Ala
        35                  40                  45

Met Gln Arg Asp Leu Gly Leu Thr Lys Gln Glu Ala Glu Gln Arg Leu
    50                  55                  60

Arg Ser Glu Ala Glu Ala Arg Glu Val His Glu Thr Val Ser Glu Arg
65                  70                  75                  80

Leu Gly Ser Asp Phe Ala Gly Ala His Tyr Asp Ala Glu Arg Gly Thr
                85                  90                  95

Leu Val Val Gly Val Thr Asp Ala Ala Glu Phe Ser Glu Val Arg Glu
            100                 105                 110

Ala Gly Ala Thr Pro Arg Leu Val Glu His Thr Val Ala Asp Leu Glu
        115                 120                 125

Ser Ala Ala Glu Lys Leu Asp Ala Lys Glu Ser Arg Ala Pro Glu Ser
    130                 135                 140

Val Thr Gly Trp Tyr Val Asp Ile Glu Ala Asn Ser Val Val Val Thr
145                 150                 155                 160

Thr Lys Pro Gly Thr Ala Gly Gln Ala Glu Arg Phe Val Ser Arg Ala
                165                 170                 175

Gly Val Asp Ala Asp Ala Val Asp Val Val Glu Ser Lys Glu Ser Pro
            180                 185                 190

Arg Ala Leu Met Asp Ile Ile Gly Gly Asn Ala Tyr Tyr Met Gly Ser
        195                 200                 205

Gly Gly Arg Cys Ser Val Gly Phe Ser Val Gln Gly Gly Phe Val Thr
    210                 215                 220

Ala Gly His Cys Gly Thr Thr Gly Thr Thr Thr Ser Ser Pro Thr Gly
225                 230                 235                 240

Arg Phe Ala Gly Ser Ser Phe Pro Gly Asn Asp Tyr Ala Phe Val Arg
                245                 250                 255

Thr Gly Ser Gly Asp Thr Leu Arg Pro Trp Val Asn Met Tyr Asn Gly
            260                 265                 270

Ser Ala Arg Val Val Ser Gly Ser Glu Ala Pro Val Gly Ser Ser
        275                 280                 285

Ile Cys Arg Ser Gly Ser Thr Thr Gly Trp His Cys Gly Thr Val Glu
    290                 295                 300

Ala Lys Asn Gln Thr Val Arg Tyr Pro Gln Gly Thr Val Tyr Gly Leu
305                 310                 315                 320

Thr Arg Thr Asn Val Cys Ala Glu Pro Gly Asp Ser Gly Gly Ser Phe
```

```
                    325                 330                 335
Ile Ser Gly Asn Gln Ala Gln Gly Met Thr Ser Gly Gly Ser Gly Asn
                340                 345                 350

Cys Thr Trp Gly Gly Thr Thr Tyr Phe Gln Pro Val Asn Glu Val Leu
                355                 360                 365

Asn Ala Tyr Gly Leu Arg Leu Ile Thr Gly
                370                 375

<210> SEQ ID NO 12
<211> LENGTH: 379
<212> TYPE: PRT
<213> ORGANISM: Saccharomonospora cyanea

<400> SEQUENCE: 12

Met Asn Arg Lys Thr Ala Ala Arg Leu Ile Ala Ser Val Thr Leu Ala
1               5                   10                  15

Ala Gly Thr Ala Met Ala Phe Thr Leu Pro Ala Thr Ala Ala Pro Ala
                20                  25                  30

Ala Pro Asp Ser Val Val Pro Thr Glu Ala Asp Pro Val Val Lys
            35                  40                  45

Ala Met Gln Arg Asp Leu Gly Leu Thr Lys Glu Gln Ala Glu Gln Arg
50                  55                  60

Leu Arg Ser Glu Ala Glu Ala Arg Lys Val His Glu Ala Val Thr Ala
65                  70                  75                  80

Asp Leu Gly Ala Asp Phe Ala Gly Ala His Tyr Asp Ala Ala Leu Gly
                85                  90                  95

Lys Leu Val Val Gly Val Thr Asp Ala Ala Glu Phe Asp Glu Val Arg
                100                 105                 110

Ala Ala Gly Ala Lys Pro Arg Leu Val Glu His Thr Val Ala Asp Leu
                115                 120                 125

Glu Gln Ala Ala Ala Leu Asp Ala Lys Glu Asn Ser Ala Pro Glu
    130                 135                 140

Ser Val Thr Gly Trp Tyr Val Asp Val Glu Ala Asn Ser Val Val Val
145                 150                 155                 160

Thr Thr Ala Val Gly Thr Ala Glu Gln Ala Glu Arg Phe Val Asp Arg
                165                 170                 175

Ala Gly Val Asp Ala Asp Ala Val Ala Val Glu Ser Lys Glu Ser
                180                 185                 190

Pro Arg Ala Leu Met Asp Ile Ile Gly Gly Asn Ala Tyr Tyr Met Gly
                195                 200                 205

Ser Gly Gly Arg Cys Ser Ile Gly Phe Ala Val Gln Gly Gly Phe Val
                210                 215                 220

Thr Ala Gly His Cys Gly Thr Thr Gly Thr Ser Thr Ser Ser Pro Thr
225                 230                 235                 240

Gly Arg Phe Ala Gly Ser Ser Phe Pro Gly Asn Asp Tyr Ala Phe Val
                245                 250                 255

Gln Thr Gly Ser Gly Asp Thr Leu Arg Pro Trp Val Asn Met Tyr Asn
                260                 265                 270

Gly Ser Ala Arg Val Val Ser Gly Ser Ser Glu Ala Pro Val Gly Ser
                275                 280                 285

Ser Val Cys Arg Ser Gly Ser Thr Thr Gly Trp His Cys Gly Thr Ile
            290                 295                 300

Gln Ala Lys Asn Gln Thr Val Arg Tyr Ala Glu Gly Thr Val Tyr Gly
305                 310                 315                 320
```

```
Leu Thr Arg Thr Asn Val Cys Ala Glu Pro Gly Asp Ser Gly Gly Ser
                325                 330                 335

Phe Ile Ser Gly Asn Gln Ala Gln Gly Met Thr Ser Gly Gly Ser Gly
            340                 345                 350

Asn Cys Thr Trp Gly Gly Thr Thr Tyr Phe Gln Pro Val Asn Glu Val
        355                 360                 365

Leu Asn Ala Tyr Gly Leu Arg Leu Ile Thr Gly
    370                 375

<210> SEQ ID NO 13
<211> LENGTH: 375
<212> TYPE: PRT
<213> ORGANISM: Saccharomonospora paurometabolica

<400> SEQUENCE: 13

Met Lys Arg Thr Arg Asn Gly Phe Ala Ala Arg Ala Gly Ala Ala Ala
1               5                   10                  15

Val Leu Ala Ala Gly Thr Ala Ala Phe Ala Leu Pro Ala Ser Ala
            20                  25                  30

Gln Pro Ala Pro Met Asp Val Asp Pro Gly Met Val Gln Ala Met Glu
        35                  40                  45

Arg Asp Leu Gly Leu Ser Gly Thr Gln Ala Glu Gln Arg Leu Arg Ser
    50                  55                  60

Glu Ala Thr Ala Arg Ala Val Asp Glu Thr Val Arg Ala Glu Leu Gly
65                  70                  75                  80

Asp Ser Phe Gly Gly Ser Phe Tyr Asp Ala Asp Lys Gly Gly Leu Val
                85                  90                  95

Val Ser Val Thr Asp Pro Ala Gln Leu Arg Glu Ala Arg Ala Ala Gly
            100                 105                 110

Ala Glu Ala Arg Met Val Asp Asp Ser Ala Ala Glu Leu Glu Ala Ala
        115                 120                 125

Ala Asn Arg Leu Asn Arg Ala Glu Ser Arg Ala Pro Gly Ser Val Thr
    130                 135                 140

Gly Trp Tyr Val Asp Val Glu Arg Asn Ser Val Val Thr Thr Thr
145                 150                 155                 160

Pro Gly Thr Ala Ala Gly Ala Glu Glu Phe Val Ala Ser Ala Gly Val
                165                 170                 175

Asp Ala Asp Thr Ala Glu Val Val Glu Ser Ala Glu Arg Pro Arg Ala
            180                 185                 190

Leu Met Asp Val Val Gly Gly Asn Ala Tyr Tyr Met Gly Ser Gly Gly
        195                 200                 205

Arg Cys Ser Val Gly Phe Ala Val Asn Gly Gly Phe Val Thr Ala Gly
    210                 215                 220

His Cys Gly Ser Thr Gly Glu Ser Thr Ser Gln Pro Ser Gly Thr Phe
225                 230                 235                 240

Ala Gly Ser Ser Phe Pro Tyr Asn Asp Tyr Ala Tyr Val Glu Thr Gly
                245                 250                 255

Ser Asp Asp Thr Pro Arg Pro Tyr Val Asn Thr Tyr Ser Gly Thr Arg
            260                 265                 270

Thr Val Ser Gly Ser Asn Glu Ala Pro Val Gly Ser Ser Ile Cys Arg
        275                 280                 285

Ser Gly Ser Thr Thr Gly Trp His Cys Gly Thr Val Glu Ala Lys Asn
    290                 295                 300

Gln Thr Val Arg Tyr Ser Gln Gly Ala Val Tyr Gly Met Thr Arg Thr
305                 310                 315                 320
```

```
Asp Val Cys Ala Glu Pro Gly Asp Ser Gly Gly Ser Phe Ile Ser Gly
            325                 330                 335

Asn Gln Ala Gln Gly Met Thr Ser Gly Gly Ser Gly Asn Cys Thr Trp
            340                 345                 350

Gly Gly Thr Thr Tyr Phe Gln Pro Val Asn Glu Ala Leu Asn Ala Tyr
        355                 360                 365

Gly Leu Ser Leu Val Thr Gly
        370             375
```

USE OF POLYPEPTIDES HAVING PROTEASE ACTIVITY IN ANIMAL FEED AND DETERGENTS

CROSS-REFERENCE TO RELATED APPLICATIONS

This application is a 35 U.S.C. 371 national application of PCT/EP2013/051448 filed Jan. 25, 2013, which claims priority or the benefit under 35 U.S.C. 119 of European application no. 12152669.3 filed Jan. 26, 2012 and U.S. provisional application No. 61/590,998 filed Jan. 26, 2012, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to the use of isolated polypeptides having protease activity in animal feed and detergents. It also relates to the use of isolated nucleic acid sequences encoding the proteases in the recombinant production of isolated polypeptides having protease activity and isolated nucleic acid sequences encoding the proteases. The invention also relates to nucleic acid constructs, vectors, and host cells, including plant and animal cells, comprising the nucleic acid sequences, as well as methods for producing and using the proteases, in particular the use of the proteases in animal feed, and detergents.

Description of the Related Art

Proteases of the S1 group and isolated from *Saccharopolyspora* are known in the art. A protease from *Saccharopolyspora erythrea* was disclosed by Oliynk et al., 2007 in 'Complete genome sequence of the erythromycin-producing bacterium *Saccharopolyspora erythraea* NRRL23338', *Nat. Biotechnol.* 25:447-453. The complete genone sequence was submitted to EMBL/GenBank under accession number AM420293. The amino acid sequence (uniprot: A4FNQ0) is identical to the sequence of SEQ ID NO: 2 (herein) and the mature amino acid sequence is disclosed in SEQ ID NO: 5.

Other S1 proteases are disclosed in the prior art, such as the protease (Uniprot: C7MV18, SEQ ID NO: 9) described by Pati et al., 2009, 'Complete genome sequence of *Saccharomonospora viridis* type strain (P101T)', Stand. Genomic Sci., 1:141-149 with a sequence identity of 80.7% to SEQ ID NO: 5. Yum et al. have described a protease (Uniprot: Q55353, SEQ ID NO: 10) in 'Purification and characterization of alkaline serine protease from an alkalophilic *Streptomyces* sp.', *Biosci. Biotechnol. Biochem.*, 58:470-474 (1994) with sequence identity of 70.4% to SEQ ID NO: 5.

Lucas et al have submitted a protease from *Saccharomonospora xinjiangensis* XJ-54 with 79.6% sequence identity to SEQ ID NO: 5 to EMBL/GenBank (Uniprot: 10V8H8, SEQ ID NO: 11) and another protease from *Saccharomonospora cyanea* NA-134 with 79.0% sequence identity to SEQ ID NO: 5 to EMBL/GenBank (Uniprot: H5XEH4, SEQ ID NO: 12). A further protease from *Saccharomonospora paurometabolica* YIM 90007 with 76.1% sequence identity to SEQ ID NO: 5 has been submitted to EMBL/GenBank (Uniprot: G4J6Q2, SEQ ID NO: 13).

In the patent literature, one protease from *Streptomyces* sp., which is identical to Uniprot: Q55353 (SEQ ID NO: 10 herein), was disclosed in WO 2005/052146 (SEQ ID NO: 649, Geneseqp: AEA48820) and another protease was disclosed in WO 2005/052161 (SEQ ID NO: 649, Geneseqp: AEA80317) both with sequence identity of 70.4% to SEQ ID NO: 5 for use in animal feed and detergent compositions. Other known proteases have sequence identities that are about or lower than 70%.

The use of proteases in animal feed to improve digestion of proteins in the feed is known. WO 2009/058679 and US 2009/0111161 relating to a protease from *Streptomyces* (Streptomyces 1AG3 protease) having an identity to the presently indicated protease of SEQ ID NO: 2 of 66%, mention the use of the protease in animal feed. WO 95/28850 discloses the combination of a phytase and one or more microbial proteolytic enzymes to improve the solubility of vegetable proteins. WO 01/58275 discloses the use of acid stable proteases of the subtilisin family in animal feed. WO 01/58276 discloses the use in animal feed of acid-stable proteases related to the protease derived from *Nocardiopsis* sp. NRRL 18262 (the 10R protease), as well as a protease derived from *Nocardiopsis alba* DSM 14010. WO 04/072221, WO 04/111220, WO 04/111223, WO 05/035747, and WO 05/123911 disclose proteases related to the 10R protease and their use in animal feed. Also, WO 04/072279 discloses the use of other proteases in animal feed.

WO 04/034776 discloses the use of a subtilisin/keratinase, PWD-1 from *B. licheniformis* in the feed of poultry. WO 04/077960 discloses a method of increasing digestibility of forage or grain in ruminants by applying a bacterial or fungal protease.

Commercial products comprising a protease and marketed for use in animal feed include RONOZYME® ProAct (DSM NP/Novozymes), Axtra® (Danisco), Avizyme® (Danisco), Porzyme® (Danisco), Allzyme™ (Alltech), Versazyme® (BioResources, Int.), Poultrygrow™ (Jefo) and Cibenza® DP100 (Novus).

SUMMARY OF THE INVENTION

Background of the Invention

In the use of proteases in animal feed (in vivo), and/or the use of such proteases for treating vegetable proteins (in vitro) it is noted that proteins are essential nutritional factors for animals and humans. Most livestock and many human beings get the necessary proteins from vegetable protein sources. Important vegetable protein sources are e.g. oilseed crops, legumes and cereals.

When e.g. soybean meal is included in the feed of mono-gastric animals such as pigs and poultry, a significant proportion of the soybean meal solids is not digested efficiently (the apparent ileal protein digestibility in piglets, growing pigs and poultry such as broilers, laying hens and roosters is only around 80%).

The gastrointestinal tract of animals consists of a series of segments each representing different pH environments. In mono-gastric animals such as pigs and poultry and many fish the stomach exhibits strongly acidic pH as low as pH 1-2, while the intestine exhibit a more neutral pH in the area pH 6-7. Poultry in addition to stomach and intestine also have a crop preceding the stomach, pH in the crop is mostly determined by the feed ingested and hence typically lies in the range pH 4-6. Protein digestion by a protease may occur along the entire digestive tract, given that the protease is active and survives the conditions in the digestive tract. Hence, proteases which are highly acid stable for survival in the gastric environment and at the same time are efficiently active at broad physiological pH of the target animal are especially desirable.

Also, animal feed is often formulated in pelleted form, where steam is applied in the pelleting process. It is therefore also desirable that proteases used in animal feed are capable to remain active after exposure to steam treatment.

Proteases have also for many years been used in detergent compositions for hydrolysing proteinaceous materials on textiles, hard surfaces and other surfaces, such as the skin, etc. Such detergent compositions can be used for the cleaning of textiles, in hand washing or in automatic machines by powders, tablets or soap bars, and in dish washing by hand or machine as powders, and tablets.

The novel S1 protease variants of the invention are also useful for these purposes.

In order to produce a protease for industrial use, it is important that the protease is produced in high yields making the product available in sufficient quantities in order to be able to provide the protease at a favourable price.

The present invention relates to the use in animal feed and detergents of isolated polypeptides having protease activity selected from the group consisting of:

(a) a polypeptide having at least 80% sequence identity to SEQ ID NO: 5;

(b) a polypeptide encoded by a polynucleotide that hybridizes under high stringency conditions or very high stringency conditions with:
 (i) the mature polypeptide coding sequence of SEQ ID NO: 1;
 (ii) the mature polypeptide coding sequence of SEQ ID NO: 3;
 (iii) the full-length complementary strand of (i) or (ii);

(c) a polypeptide encoded by a polynucleotide having at least 80% sequence identity to the mature polypeptide coding sequence of SEQ ID NO: 1 or SEQ ID NO: 3;

(d) a variant comprising a substitution, deletion, and/or insertion of one or more (several) amino acids of SEQ ID NO: 5; and (e) a fragment of a polypeptide of (a), (b), (c) or (d), that has protease activity.

The present invention also relates to variant polypeptides having protease activity and having at least 85% sequence identity to SEQ ID NO: 5 comprising at least one substitution, deletion, and/or insertion of at least one or more (several) amino acids of SEQ ID NO: 5 or homologous sequences.

The present invention also relates to isolated polynucleotides encoding the polypeptides of the present invention, nucleic acid constructs, recombinant expression vectors, and recombinant host cells comprising the polynucleotides, and to methods of recombinantly producing the polypeptides.

The present invention also relates to methods for preparing a composition for use in animal feed, for improving the nutritional value of an animal feed, and methods of treating proteins to be used in animal feed compositions.

Furthermore the present invention also relates to detergent compositions comprising the proteases.

OVERVIEW OF SEQUENCE LISTING

Figure 1:
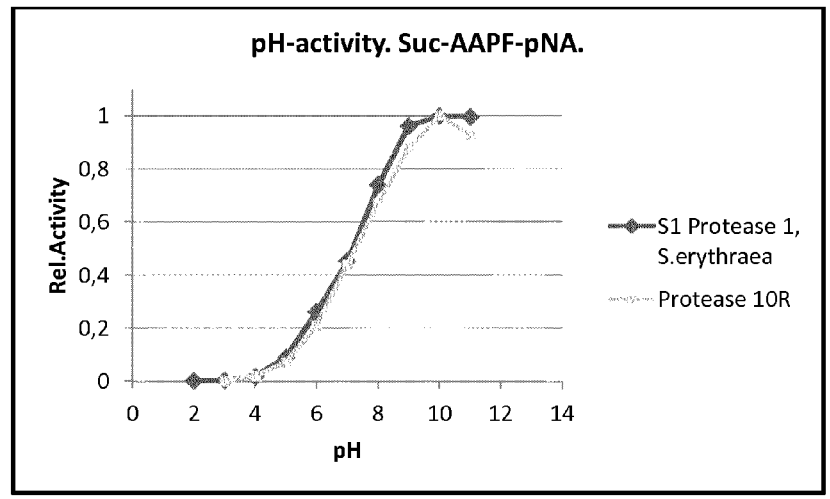
FIG. 1 shows the pH-activity profile on the Suc-AAPF-pNA substrate for the S1 Protease 1 from *Saccharomonospora erythraea* compared to the 10R protease.
Figure 2:
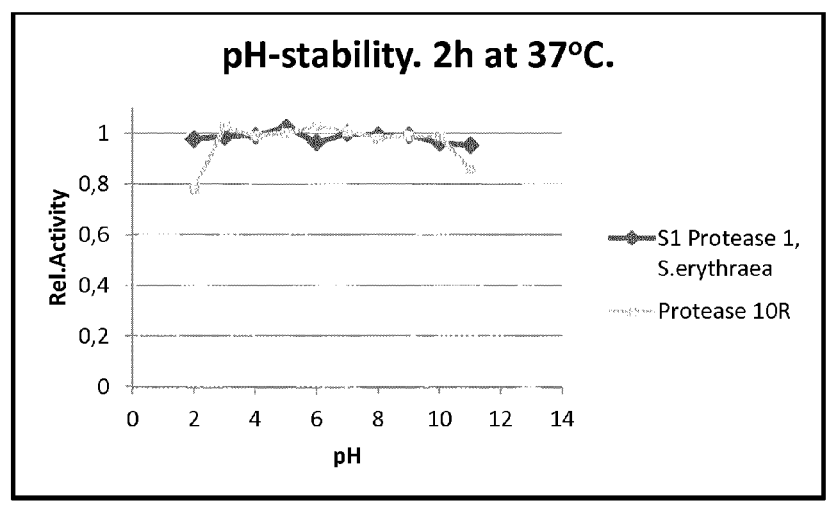
FIG. 2 shows the pH-stability profile (residual activity after 2 hours at 37° C. for the S1 Protease 1 from *Saccharomonospora erythraea* compared to the 10R protease, FIG. 3 shows the temperature activity profile on Protazyme AK at pH 7.0 for the S1 Protease 1 from *Saccharomonospora erythraea* compared to the 10R protease, FIG. 4 shows the P1-specificity on 10 Suc-AAPF-pNA substrates at pH 9.0 for the S1 Protease 1 from *Saccharomonospora erythraea* compared to the 10R protease.
Figure 3:
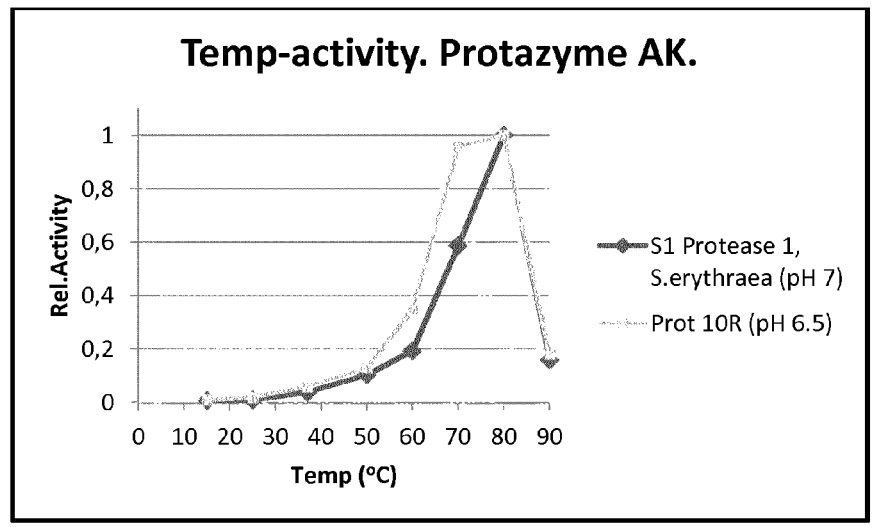
Figure 4:
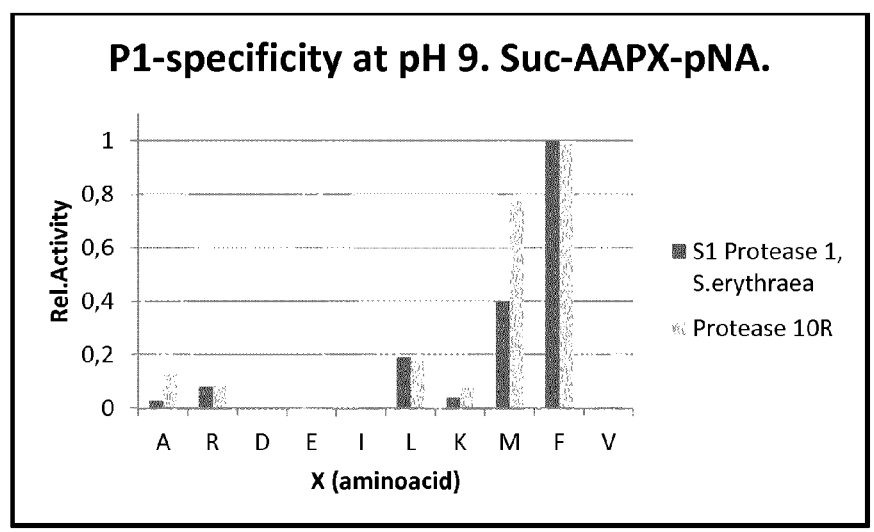

SEQ ID NO: 1 is the DNA sequence as isolated from *Saccharopolyspora erythrea*.

SEQ ID NO: 2 is the amino acid sequence as deduced from SEQ ID NO: 1.

SEQ ID NO: 3 is a synthetic DNA sequence used for recombinant production of the S1 protease 1 from *Saccharopolyspora erythrea*.

SEQ ID NO: 4 is the amino acid sequence as deduced from SEQ ID NO: 3.

SEQ ID NO: 5 is the amino acid sequence of the mature S1 protease 1 from *Saccharopolyspora erythrea*.

SEQ ID NO: 6 is a *Bacillus lentus* secretion signal.

SEQ ID NO: 7 is the DNA sequence of the 10R protease (WO 05/035747, SEQ ID NO: 1).

SEQ ID NO: 8 is the amino acid sequence of the 10R protease (WO 05/035747, SEQ ID NO: 2).

SEQ ID NO: 9 is the amino acid sequence of a serine protease from *Saccharomonospora viridis* (UNIPROT: C7MV18).

SEQ ID NO: 10 is the amino acid sequence of a serine protease from *Streptomyces* sp. (UNIPROT: Q55353).

SEQ ID NO: 11 is the amino acid sequence of a serine protease from *Saccharomonospora xinjiangensis* XJ-54 (UNIPROT: I0V8H8).

SEQ ID NO: 12 is the amino acid sequence of a serine protease from *Saccharomonospora cyanea* NA-134 (UNIPROT: H5XEH4).

SEQ ID NO: 13 is the amino acid sequence of a serine protease from *Saccharomonospora paurometabolica* YIM 90007 (UNIPROT: G4J6Q2).

Identity Matrix of Sequences

| | SEQ ID NO: 2 | SEQ ID NO: 4 | SEQ ID NO: 5 | SEQ ID NO: 8 | SEQ ID NO: 9 | SEQ ID NO: 10 | SEQ ID NO: 11 | SEQ ID NO: 12 | SEQ ID NO: 13 |
|---|---|---|---|---|---|---|---|---|---|
| SEQ ID NO: 2 | 100 | 95.2 | 100 | 48.5 | 63.2 | 56.5 | 61.1 | 62.6 | 63.4 |
| SEQ ID NO: 4 | 95.2 | 100 | 100 | 47.7 | 61.5 | 55.5 | 60.4 | 61.5 | 61.2 |

-continued

|  | SEQ ID NO: 2 | SEQ ID NO: 4 | SEQ ID NO: 5 | SEQ ID NO: 8 | SEQ ID NO: 9 | SEQ ID NO: 10 | SEQ ID NO: 11 | SEQ ID NO: 12 | SEQ ID NO: 13 |
|---|---|---|---|---|---|---|---|---|---|
| SEQ ID NO: 5 | 100 | 100 | 100 | 58.3 | 80.7 | 70.4 | 79.6 | 79.0 | 76.1 |
| SEQ ID NO: 8 | 48.5 | 47.7 | 58.3 | 100 | 50.0 | 50.8 | 49.7 | 51.2 | 48.5 |
| SEQ ID NO: 9 | 63.2 | 61.5 | 80.7 | 50.0 | 100 | 54.9 | 73.8 | 73.3 | 70.1 |
| SEQ ID NO: 10 | 56.5 | 55.5 | 70.4 | 50.8 | 54.9 | 100 | 56.1 | 55.0 | 54.4 |
| SEQ ID NO: 11 | 61.1 | 60.4 | 79.6 | 49.7 | 73.8 | 56.1 | 100 | 89.4 | 73.1 |
| SEQ ID NO: 12 | 62.6 | 61.5 | 79.0 | 51.2 | 73.3 | 55.0 | 89.4 | 100 | 72.5 |
| SEQ ID NO: 13 | 63.4 | 61.2 | 76.1 | 48.5 | 70.1 | 54.4 | 73.1 | 72.5 | 100 |

DEFINITIONS

Polypeptides Having Protease Activity

Polypeptides having protease activity, or proteases, are sometimes also designated peptidases, proteinases, peptide hydrolases, or proteolytic enzymes. Proteases may be of the exo-type that hydrolyse peptides starting at either end thereof or of the endo-type that act internally in polypeptide chains (endopeptidases). Endopeptidases show activity on N- and C-terminally blocked peptide substrates that are relevant for the specificity of the protease in question.

The term "protease" is defined herein as an enzyme that hydrolyses peptide bonds. This definition of protease also applies to the protease-part of the terms "parent protease" and "protease variant," as used herein. The term "protease" includes any enzyme belonging to the EC 3.4 enzyme group (including each of the thirteen subclasses thereof). The EC number refers to Enzyme Nomenclature 1992 from NC-IUBMB, Academic Press, San Diego, Calif., including supplements 1-5 published in Eur. J. Bio-chem. 1994, 223, 1-5; Eur. J. Biochem. 1995, 232, 1-6; Eur. J. Biochem. 1996, 237, 1-5; Eur. J. Biochem. 1997, 250, 1-6; and Eur. J. Biochem. 1999, 264, 610-650; respectively. The nomenclature is regularly supplemented and updated; see e.g. the World Wide Web (WWW) at chem.qmw.ac.uk/iubmb/enzyme/index.html.

The present invention provides for the use of polypeptides having protease activity in animal feed and detergent compositions. It also provides polypeptides having protease activity and polynucleotides encoding the polypeptides. The proteases of the invention are serine proteases of the peptidase family S1. The proteases of the invention exhibit surprising pH properties, especially pH stability properties which makes them interesting candidates for use in animal feed. The proteases of the invention thus are active on Suc-Ala-Ala-Pro-Phe-pNA within a broad range from pH 4-11 and exhibit especially high activity in the range pH 6-11, are active on a feed relevant soybean meal-maize meal substrate within a broad physiological pH range from pH 3-7 and retains more than 80% activity after being subjected for 2 hours to pH as low as 2.

The proteases of the invention and for use according to the invention are selected from the group consisting of:
(a) proteases belonging to the EC 3.4.21 enzyme group; and/or
(b) Serine proteases of the peptidase family S1;
as described in Biochem. J. 290:205-218 (1993) and in MEROPS protease database, release, 9.4 (31 Jan. 2011) (merops.ac.uk). The database is described in Rawlings, N. D., Barrett, A. J. & Bateman, A. (2010) 'MEROPS: the peptidase database', Nucleic Acids Res 38, D227-D233.

Proteases of the invention are endopeptidases (EC 3.4.21). There are several protease activity types: The three main activity types are: trypsin-like where there is cleavage of amide substrates following Arg or Lys at P1, chymotrypsin-like where cleavage occurs following one of the hydrophobic amino acids at P1, and elastase-like with cleavage following an Ala at P1.

The polypeptides of the present invention have at least 20%, e.g., at least 40%, at least 50%, at least 60%, at least 70%, at least 80%, at least 90%, at least 95%, and at least 100% of the protease activity of the SEQ ID NO: 5 or mature polypeptide of SEQ ID NO: 2 or SEQ ID NO: 4.

More specifically the proteases used in the invention are those that prefer a hydrophobic aromatic amino acid residue in the P1 position.

For determining whether a given protease is a serine protease, and a family S1 protease, reference is made to the above Handbook and the principles indicated therein. Such determination can be carried out for all types of proteases, be it naturally occurring or wild-type proteases; or genetically engineered or synthetic proteases.

The peptidases of family S1 contain the catalytic triad His, Asp and Ser in that order. Mutation of any of the amino acids of the catalytic triad will result in change or loss of enzyme activity. The amino acids of the catalytic triad of the S1 protease 1 as isolated from Saccharopolyspora erythrea (SEQ ID NO: 5) are probably positions His-35, Asp-63 and Ser-144.

Protease activity can be measured using any assay, in which a substrate is employed, that includes peptide bonds relevant for the specificity of the protease in question. Assay-pH and assay-temperature are likewise to be adapted to the protease in question. Examples of assay-pH-values are pH 2, 3, 4, 5, 6, 7, 8, 9, 10, 11, or 12. Examples of assay-temperatures are 15, 20, 25, 30, 35, 37, 40, 45, 50, 55, 60, 65, 70, 80, 90, or 95° C. Examples of general protease substrates are casein, bovine serum albumin and haemoglobin. In the classical Anson and Mirsky method, denatured haemoglobin is used as substrate and after the assay incubation with the protease in question, the amount of trichloroacetic acid soluble haemoglobin is determined as a measurement of protease activity (Anson, M. L. and Mirsky, A. E., 1932, J. Gen. Physiol. 16: 59 and Anson, M. L., 1938, J. Gen. Physiol. 22: 79).

For the purpose of the present invention, protease activity was determined using assays which are described in "Materials and Methods", such as the Kinetic Suc-AAPF-pNA assay, Protazyme AK assay, Kinetic Suc-AAPX-pNA assay and o-Phthaldialdehyde (OPA). For the Protazyme AK assay, insoluble Protazyme AK (Azurine-Crosslinked Casein) substrate liberates a blue colour when incubated with the protease and the colour is determined as a measurement of protease activity. For the Suc-AAPF-pNA assay, the colourless Suc-AAPF-pNA substrate liberates yellow paranitroaniline when incubated with the protease and the yellow colour is determined as a measurement of protease activity.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

cDNA: The term "cDNA" means a DNA molecule that can be prepared by reverse transcription from a mature, spliced, mRNA molecule obtained from a eukaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant polynucleotide.

Control sequences: The term "control sequences" means all components necessary for the expression of a polynucleotide encoding a polypeptide of the present invention. Each control sequence may be native or foreign to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of the polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to additional nucleotides that provide for its expression.

Fragment: The term "fragment" means a polypeptide having one or more (several) amino acids deleted from the amino and/or carboxyl terminus of a mature polypeptide; wherein the fragment has protease activity. In one aspect, a fragment contains at least 169 amino acid residues (e.g., amino acids 10 to 178 of SEQ ID NO: 2), or at least 179 amino acid residues (e.g., amino acids 5 to 183 of SEQ ID NO: 2); or correspondingly for SEQ ID NO: 4 a fragment contains at least 169 amino acid residues (e.g., amino acids 10 to 178 of SEQ ID NO: 4), or at least 179 amino acid residues (e.g., amino acids 5 to 183 of SEQ ID NO: 4); or correspondingly for SEQ ID NO: 5 a fragment contains at least 169 amino acid residues (e.g., amino acids 10 to 178 of SEQ ID NO: 5), or at least 179 amino acid residues (e.g., amino acids 5 to 183 of SEQ ID NO: 5).

Host cell: The term "host cell" means any cell type that is susceptible to transformation, transfection, transduction, and the like with a nucleic acid construct or expression vector comprising a polynucleotide of the present invention. The term "host cell" encompasses any progeny of a parent cell that is not identical to the parent cell due to mutations that occur during replication.

Isolated polynucleotide: The term "isolated polynucleotide" means a polynucleotide that is modified by the hand of man relative to that polynucleotide as found in nature. In one aspect, the isolated polynucleotide is at least 1% pure, e.g., at least 5% pure, more at least 10% pure, at least 20% pure, at least 40% pure, at least 60% pure, at least 80% pure, at least 90% pure, and at least 95% pure, as determined by agarose electrophoresis. The polynucleotides may be of genomic, cDNA, RNA, semisynthetic, synthetic origin, or any combinations thereof.

Isolated polypeptide: The term "isolated polypeptide" means a polypeptide that is modified by the hand of man relative to that polypeptide as found in nature in admixture with other components, such as other polypeptides, secondary metabolites, salts, et alia. In one aspect, the polypeptide is at least 1% pure, e.g., at least 5% pure, at least 10% pure, at least 20% pure, at least 40% pure, at least 60% pure, at least 80% pure, and at least 90% pure, as determined by SDS-PAGE.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 1 to 190 of SEQ ID NO: 2 based on the SignalP (Nielsen et al., 1997, *Protein Engineering* 10:1-6) prediction program that also predicts −183 to −157 of SEQ ID NO: 2 are a signal peptide. In another aspect, the mature polypeptide is amino acids 1 to 190 of SEQ ID NO: 4 based on sequencing using Edman degredation and intact molecular weight analysis. Amino acids −184 to −157 of SEQ ID NO: 4 is the Savinase signal peptide. It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide having protease activity. In one aspect, the mature polypeptide coding sequence is nucleotides 553 to 1122 of SEQ ID NO: 1 based on the SignalP (Nielsen et al., 1997, *Protein Engineering* 10:1-6) prediction program that also predicts nucleotides 1 to 84 of SEQ ID NO: 1 encode a signal peptide. In another aspect, the mature polypeptide coding sequence is nucleotides 550 to 1119 of SEQ ID NO: 3 based on sequencing using Edman degredation and intact molecular weight analysis of the mature polypeptide. Nucleotides 1 to 81 of SEQ ID NO: 3 encode the Savinase signal peptide.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Operably linked: The term "operably linked" means a configuration in which a control sequence is placed at an appropriate position relative to the coding sequence of a polynucleotide such that the control sequence directs the expression of the coding sequence.

Sequence Identity: The relatedness between two amino acid sequences or between two nucleotide sequences is described by the parameter "sequence identity".

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, Trends Genet. 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of Alignment−Total Number of Gaps in Alignment)

Stringency conditions: The different stringency conditions are defined as follows.

The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Subsequence: The term "subsequence" means a polynucleotide having one or more (several) nucleotides deleted from the 5' and/or 3' end of a mature polypeptide coding sequence; wherein the subsequence encodes a fragment having protease activity. In one aspect, a subsequence contains at least 507 nucleotides (e.g., nucleotides 580 to 1086 of SEQ ID NO: 1), or at least 537 nucleotides (e.g., nucleotides 565 to 1101 of SEQ ID NO: 1). In another aspect, a subsequence contains at least 507 nucleotides (e.g., nucleotides 577 to 1083 of SEQ ID NO: 3), or at least 537 nucleotides (e.g., nucleotides 562 to 1098 of SEQ ID NO: 3).

Substantially pure polynucleotide: The term "substantially pure polynucleotide" means a polynucleotide preparation free of other extraneous or unwanted nucleotides and in a form suitable for use within genetically engineered polypeptide production systems. Thus, a substantially pure polynucleotide contains at most 10%, at most 8%, at most 6%, at most 5%, at most 4%, at most 3%, at most 2%, at most 1%, and at most 0.5% by weight of other polynucleotide material with which it is natively or recombinantly associated. A substantially pure polynucleotide may, however, include naturally occurring 5' and 3' untranslated regions, such as promoters and terminators. Preferably, the polynucleotide is at least 90% pure, e.g., at least 92% pure, at least 94% pure, at least 95% pure, at least 96% pure, at least 97% pure, at least 98% pure, at least 99% pure, and at least 99.5% pure by weight. The polynucleotides of the present invention are preferably in a substantially pure form.

Substantially pure polypeptide: The term "substantially pure polypeptide" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the polypeptide is at least 92% pure, e.g., at least 94% pure, at least 95% pure, at least 96% pure, at least 97% pure, at least 98% pure, at least 99%, at least 99.5% pure, and 100% pure by weight of the total polypeptide material present in the preparation. The polypeptides of the present invention are preferably in a substantially pure form. This can be accomplished, for example, by preparing the polypeptide by well known recombinant methods or by classical purification methods.

Variant: The term "variant" means a polypeptide having protease activity and having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99% sequence identity to SEQ ID NO: 5, comprising an alteration, i.e., a substitution, insertion, and/or deletion of one or more (several) amino acid residues at one or more (several) positions. A substitution means a replacement of an amino acid occupying a position with a different amino acid; a deletion means removal of e.g. 1-5 amino acid residues occupying 1-5 positions; and an insertion means adding e.g. 1-5 amino acids adjacent to an amino acid occupying a position. The variants of the present invention have at least 20%, e.g., at least 40%, at least 50%, at least 60%, at least 70%, at least 80%, at least 90%, at least 95%, or at least 100% of the protease activity of the polypeptide of SEQ ID NO: 5. A variant may also be a naturally occurring protease having at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO: 5.

DETAILED DESCRIPTION OF THE INVENTION

Polypeptides Having Protease Activity

The present invention relates to the use in animal feed or detergents of isolated polypeptides having protease activity selected from the group consisting of:

(a) a polypeptide having at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 5;

(b) a polypeptide encoded by a polynucleotide that hybridizes under high stringency conditions, or very high stringency conditions with
  (i) the mature polypeptide coding sequence of SEQ ID NO: 1;
  (ii) the mature polypeptide coding sequence of SEQ ID NO: 3;
  (iii) the full-length complementary strand of (i) or (ii);

(c) a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the mature polypeptide coding sequence of SEQ ID NO: 1 or SEQ ID NO: 3; and/or (d) a variant comprising a substitution, deletion, and/or insertion of one or more (several) amino acids of SEQ ID NO: 5; and (e) a fragment of a polypeptide of (a), (b), (c) or (d), that has protease activity.

The present invention relates to the use in animal feed or detergents of isolated polypeptides having a sequence identity to the mature polypeptide of SEQ ID NO: 2 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have protease activity. In one aspect, the polypeptides differ by no more than thirtysix amino acids, e.g., by thirty amino acids, by twentyfive amino acids, by twenty amino acids, by fifteen amino acids, by ten amino acids, by nine amino acids, by eight amino acids, by seven amino acids, by six amino acids, by five amino acids, by four amino acids, by three amino acids, by two amino acids, and by one amino acid from the mature polypeptide of SEQ ID NO: 2.

The present invention also relates to the use in animal feed or detergents of isolated polypeptides having a sequence identity to the mature polypeptide of SEQ ID NO: 4 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have protease activity. In one aspect, the polypeptides differ by no than thirtysix amino acids, e.g., by thirty amino acids, by twentyfive amino acids, by twenty amino acids, by fifteen amino acids, by ten amino acids, by nine amino acids, by eight amino acids, by seven amino acids, by six amino acids, by five amino acids, by four amino acids, by three amino acids, by two amino acids, and by one amino acid from the mature polypeptide of SEQ ID NO: 4.

The present invention further relates to the use in animal feed or detergents of isolated polypeptides having a sequence identity to the mature polypeptide of SEQ ID NO: 5 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have protease activity. In one aspect, the polypeptides differ by no more than thirtysix amino acids, e.g., by thirty amino acids, by twentyfive amino acids, by twenty amino acids, by fifteen amino acids, by ten amino acids, by nine amino acids, by eight amino acids, by seven amino acids, by six amino acids, by five amino acids, by four amino acids, by three amino acids, by two amino acids, and by one amino acid from the mature polypeptide of SEQ ID NO: 5.

An embodiment of the invention is a polypeptide or a polypeptide encoded by a polynucleotide for use in animal feed or detergents having at least 80% sequence identity to the polypeptide of SEQ ID NO: 5.

An embodiment of the invention is a polypeptide or a polypeptide encoded by a polynucleotide for use in animal feed or detergents having at least 82% sequence identity to the polypeptide of SEQ ID NO: 5.

An embodiment of the invention is a polypeptide or a polypeptide encoded by a polynucleotide for use in animal feed or detergents having at least 84% sequence identity to the polypeptide of SEQ ID NO: 5.

An embodiment of the invention is a polypeptide or a polypeptide encoded by a polynucleotide for use in animal feed or detergents having at least 85% sequence identity to the polypeptide of SEQ ID NO: 5.

An embodiment of the invention is a polypeptide or a polypeptide encoded by a polynucleotide for use in animal feed or detergents having at least 86% sequence identity to the polypeptide of SEQ ID NO: 5.

An embodiment of the invention is a polypeptide or a polypeptide encoded by a polynucleotide for use in animal feed or detergents having at least 87% sequence identity to the polypeptide of SEQ ID NO: 5.

An embodiment of the invention is a polypeptide or a polypeptide encoded by a polynucleotide for use in animal feed or detergents having at least 88% sequence identity to the polypeptide of SEQ ID NO: 5.

An embodiment of the invention is a polypeptide or a polypeptide encoded by a polynucleotide for use in animal feed or detergents having at least 89% sequence identity to the polypeptide of SEQ ID NO: 5.

An embodiment of the invention is a polypeptide or a polypeptide encoded by a polynucleotide for use in animal feed or detergents having at least 90% sequence identity to the polypeptide of SEQ ID NO: 5.

An embodiment of the invention is a polypeptide or a polypeptide encoded by a polynucleotide for use in animal feed or detergents having at least 91% sequence identity to the polypeptide of SEQ ID NO: 5.

An embodiment of the invention is a polypeptide or a polypeptide encoded by a polynucleotide for use in animal feed or detergents having at least 92% sequence identity to the polypeptide of SEQ ID NO: 5.

An embodiment of the invention is a polypeptide or a polypeptide encoded by a polynucleotide for use in animal feed or detergents having at least 93% sequence identity to the polypeptide of SEQ ID NO: 5.

An embodiment of the invention is a polypeptide or a polypeptide encoded by a polynucleotide for use in animal feed or detergents having at least 94% sequence identity to the polypeptide of SEQ ID NO: 5.

An embodiment of the invention is a polypeptide or a polypeptide encoded by a polynucleotide for use in animal feed or detergents having at least 95% sequence identity to the polypeptide of SEQ ID NO: 5.

An embodiment of the invention is a polypeptide or a polypeptide encoded by a polynucleotide for use in animal feed or detergents having at least 96% sequence identity to the polypeptide of SEQ ID NO: 5.

An embodiment of the invention is a polypeptide or a polypeptide encoded by a polynucleotide for use in animal feed or detergents having at least 97% sequence identity to the polypeptide of SEQ ID NO: 5.

An embodiment of the invention is a polypeptide or a polypeptide encoded by a polynucleotide for use in animal feed or detergents having at least 98% sequence identity to the polypeptide of SEQ ID NO: 5.

An embodiment of the invention is a polypeptide or a polypeptide encoded by a polynucleotide for use in animal feed or detergents having at least 99% sequence identity to the polypeptide of SEQ ID NO: 5.

An embodiment of the invention is a polypeptide or a polypeptide encoded by a polynucleotide for use in animal feed or detergents having 100% sequence identity to the polypeptide of SEQ ID NO: 5.

A polypeptide to be used in the present invention preferably comprises or consists of the amino acid sequence of SEQ ID NO: 2, SEQ ID NO: 4 and/or SEQ ID NO: 5 or an allelic variant thereof; or is a fragment missing e.g. 30, 25, 20, 15, 10 or 5 amino acids from the N- and/or C-terminal and having protease activity. In another aspect, the polypeptide comprises or consists of SEQ ID NO: 2, SEQ ID NO: 4 and/or SEQ ID NO: 5. In another preferred aspect, the polypeptide comprises or consists of amino acids 1 to 190 of SEQ ID NO: 2, amino acids 1 to 190 of SEQ ID NO: 4, and/or amino acids 1 to 190 of SEQ ID NO: 5.

The present invention also relates to isolated polypeptides having protease activity that are encoded by polynucleotides that hybridize under high stringency conditions, or very high stringency conditions with (i) the mature polypeptide coding sequence of SEQ ID NO: 1, (ii) the mature polypeptide coding sequence of SEQ ID NO: 3, or (iii) the full-length complementary strand of (i) or (ii) (J. Sambrook, E. F. Fritsch, and T. Maniatis, 1989, *Molecular Cloning, A Laboratory Manual*, 2d edition, Cold Spring Harbor, N.Y.).

The polynucleotide of SEQ ID NO: 1 and/or SEQ ID NO: 3; or a subsequence thereof, as well as the amino acid sequence of SEQ ID NO: 2, SEQ ID NO: 4 and/or SEQ ID NO: 5, or a fragment thereof, may be used to design nucleic acid probes to identify and clone DNA encoding polypeptides having protease activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such other strains may be screened for DNA that hybridizes with the probes described above and encodes a polypeptide having protease activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1 or SEQ ID NO: 3; or a subsequence thereof, the carrier material is preferably used in a Southern blot.

For purposes of the present invention, hybridization indicates that the polynucleotide hybridizes to a labeled nucleic acid probe corresponding to the mature polypeptide coding sequence of SEQ ID NO: 1; the mature polypeptide coding sequence of SEQ ID NO: 3; its full-length complementary strand; or a subsequence thereof; under high to very high stringency conditions. Molecules to which the nucleic acid probe hybridizes under these conditions can be detected using, for example, X-ray film.

In one aspect, the nucleic acid probe is the mature polypeptide coding sequence of SEQ ID NO: 1 or SEQ ID NO: 3. In another aspect, the nucleic acid probe is a fragment thereof. In another aspect, the nucleic acid probe is a polynucleotide that encodes the polypeptide of SEQ ID NO: 2, SEQ ID NO: 4 and/or SEQ ID NO: 5 or a fragment thereof. In another preferred aspect, the nucleic acid probe is SEQ ID NO: 1 or SEQ ID NO: 3.

For long probes of at least 100 nucleotides in length, high to very high stringency conditions are defined as prehybridization and hybridization at 42° C. in 5×SSPE, 0.3% SDS, 200 micrograms/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally. The carrier material is finally washed three times each for 15 minutes using 2×SSC, 0.2% SDS at 65° C. (high stringency), and at 70° C. (very high stringency).

For short probes of about 15 nucleotides to about 70 nucleotides in length, stringency conditions are defined as prehybridization and hybridization at about 5° C. to about 10° C. below the calculated $T_m$ using the calculation according to Bolton and McCarthy (1962, *Proc. Natl. Acad. Sci. USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally. The carrier material is finally washed once in 6×SCC plus 0.1% SDS for 15 minutes and twice each for 15 minutes using 6×SSC at 5° C. to 10° C. below the calculated $T_m$.

The present invention also relates to the use in animal feed or detergents of isolated polypeptides having protease activity encoded by polynucleotides having a sequence identity to the mature polypeptide coding sequence of SEQ ID NO: 1 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%.

The present invention further relates to the use in animal feed or detergents of isolated polypeptides having protease activity encoded by polynucleotides having a sequence identity to the mature polypeptide coding sequence of SEQ ID NO: 3 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%.

In particular embodiments, the parent proteases and/or the protease variants of the invention and for use according to the invention are selected from the group consisting of:

(a) Proteases belonging to the EC 3.4.21 enzyme group; and (b) Serine proteases of peptidase family S1; as described in Biochem. J. 290:205-218 (1993) and in MEROPS protease database, release 9.5 (merops.ac.uk). The database is described in Rawlings, N. D., Barrett, A. J. & Bateman, A. (2010) MEROPS: the peptidase database. *Nucleic Acids Res* 38, D227-D233.

For determining whether a given protease is a serine protease, and a family S1 protease, reference is made to the above Handbook and the principles indicated therein. Such determination can be carried out for all types of proteases, be it naturally occurring or wild-type proteases; or genetically engineered or synthetic proteases.

The present invention also relates to variant polypeptides having protease activity and having at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO: 5 comprising at least one substitution, deletion, and/or insertion of at least one or more (several) amino acids of SEQ ID NO: 5 or a homologous sequence thereof.

The variant polypeptide of the invention may in one embodiment have at least 86% sequence identity to SEQ ID NO: 5.

The variant polypeptide of the invention may in one embodiment have at least 87% sequence identity to SEQ ID NO: 5.

The variant polypeptide of the invention may in one embodiment have at least 88% sequence identity to SEQ ID NO: 5.

The variant polypeptide of the invention may in one embodiment have at least 89% sequence identity to SEQ ID NO: 5.

The variant polypeptide of the invention may in one embodiment have at least 90% sequence identity to SEQ ID NO: 5.

The variant polypeptide of the invention may in one embodiment have at least 91% sequence identity to SEQ ID NO: 5.

The variant polypeptide of the invention may in one embodiment have at least 92% sequence identity to SEQ ID NO: 5.

The variant polypeptide of the invention may in one embodiment have at least 93% sequence identity to SEQ ID NO: 5.

The variant polypeptide of the invention may in one embodiment have at least 94% sequence identity to SEQ ID NO: 5.

The variant polypeptide of the invention may in one embodiment have at least 95% sequence identity to SEQ ID NO: 5.

The variant polypeptide of the invention may in one embodiment have at least 96% sequence identity to SEQ ID NO: 5.

The variant polypeptide of the invention may in one embodiment have at least 97% sequence identity to SEQ ID NO: 5.

The variant polypeptide of the invention may in one embodiment have at least 98% sequence identity to SEQ ID NO: 5.

The variant polypeptide of the invention may in one embodiment have at least 99% sequence identity to SEQ ID NO: 5.

In a further embodiment, the total number of positions of the variant polypeptide of the invention (SEQ ID NO: 5) having amino acid substitutions, deletions and/or insertions is not more than 27, e.g., 1, 2, 3, 4, 5, 6, 7, 8, 9, 10, 11, 12, 13, 14, 15, 16, 17, 18, 19, 20, 21, 22, 23, 24, 25, 26 or 27. The amino acid changes may be of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

In another embodiment, the present invention also relates to variants for use in animal feed or detergents comprising a substitution, deletion, and/or insertion of one or more (or several) amino acids of SEQ ID NO: 2 or a homologous sequence thereof. The total number of positions having amino acid substitutions, deletions and/or insertions in SEQ ID NO: 2 is not more than 36, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or 36. The amino acid changes may be of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

In another embodiment, the present invention also relates to variants for use in animal feed or detergents comprising a substitution, deletion, and/or insertion of one or more (or several) amino acids of SEQ ID NO: 4 or a homologous sequence thereof. The total number of positions having amino acid substitutions, deletions and/or insertions in SEQ ID NO: 4 is not more than 36, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or 36. The amino acid changes may be of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

In another embodiment, the present invention also relates to variants for use in animal feed or detergents comprising a substitution, deletion, and/or insertion of one or more (or several) amino acids of SEQ ID NO: 5 or a homologous sequence thereof. The total number of positions having amino acid substitutions, deletions and/or insertions in SEQ ID NO: 5 is not more than 36, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or 36. The amino acid changes may be of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like. Essential amino acids in a parent polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for protease activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identities of essential amino acids can also be inferred from analysis of identities with polypeptides that are related to the parent polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochemistry 30: 10832-10837; U.S. Pat. No. 5,223,409; WO 92/06204), and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be hybrid polypeptide in which a portion of one polypeptide is fused at the N-terminus or the C-terminus of a portion of another polypeptide.

The polypeptide may be a fused polypeptide or cleavable fusion polypeptide in which another polypeptide is fused at the N-terminus or the C-terminus of the polypeptide of the present invention. A fused polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fused polypeptide is under control of the same promoter(s) and terminator. Fusion proteins may also be constructed using intein technology in which fusions are created post-translationally (Cooper et al., 1993, EMBO J. 12: 2575-2583; Dawson et al., 1994, Science 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, J. Ind. Microbiol. Biotechnol. 3: 568-576; Svetina et al., 2000, J. Biotechnol. 76: 245-251; Rasmussen-Wilson et al., 1997, Appl. Environ. Microbiol. 63: 3488-3493; Ward et al., 1995, Biotechnology 13: 498-503; and Contreras et al., 1991, Biotechnology 9: 378-381; Eaton et al., 1986, Biochemistry 25: 505-512; Collins-Racie et al., 1995, Biotechnology 13: 982-987; Carter et al., 1989, Proteins: Structure, Function, and Genetics 6: 240-248; and Stevens, 2003, Drug Discovery World 4: 35-48.

Embodiments

In certain embodiments of the invention, the protease of the invention exhibits beneficial thermal properties such as thermostability, steam stability, etc and/or beneficial pH properties, such as acid stability, pH optimum, etc.

An embodiment of the invention is isolated polypeptides for use in animal feed and detergents having improved protease activity between pH 6 and 9, such as at pH 6, such as at pH 8, such as at pH 9 at 25° C. compared to protease 10R.

A further embodiment of the invention is isolated polypeptides for use in animal feed and detergents having improved stability at pH 2 or at pH 11 at 37° C. compared to protease 10R. An additional embodiment of the invention is isolated polypeptides for use in animal feed and detergents having improved protease activity on soybean-maze meal between pH 3.0 and 7.0, such as between pH 5.0 and pH 7.0, such as at pH 5.0, 6.0 or 7.0 at 40° C. compared to protease 10R.

Another embodiment of the invention is isolated polypeptides for use in animal feed and detergents having improved proteolytic activity of broiler digesta expressed as the level of primary amines in the crop after 3 hours when compared to blank.

Acidity/Alkalinity Properties

In certain embodiments of the invention the protease of the invention exhibits beneficial properties in respect of pH, such as acid stability, pH optimum, etc. Stability of the protease at a low pH is beneficial since the protease can have activity in the intestine after passing through the stomach. In one embodiment of the invention the protease retains >95% activity after 2 hours at pH 2 as determined using the method described in Example 3.

pH-Activity Properties

The pH-activity profile of the protease may be determined as described in Example 3. Activity at pH 6-8 can be advantageous for the digestion of proteins in the intestine of an animal.

In one embodiment, the invention comprises of a protease for use in animal feed having a pH-activity profile at 25° C. with relative activity of 0.7 or higher at pH 8 when compared to the activity of the protease at pH 10 (cf. Example 3).

Thermostability

Thermostability may be determined as described in Example 6, i.e. using DSC measurements to determine the denaturation temperature, $T_d$, of the purified protease protein. The Td is indicative of the thermostability of the protein: The higher the $T_d$, the higher the thermostability. Accordingly, in a preferred embodiment, the protease of the invention has a $T_d$ which is higher than the $T_d$ of a reference protease, wherein $T_d$ is determined on purified protease samples (preferably with a purity of at least 90% or 95%, as determined by SDS-PAGE).

In preferred embodiments, the thermal properties such as heat-stability, temperature stability, thermostability, steam stability, and/or pelleting stability as provided by the residual activity, denaturation temperature $T_d$, or other parameter of the protease of the invention is higher than the corresponding value, such as the residual activity or $T_d$, of the protease of SEQ ID NO: 5, more preferably at least 101% thereof, or at least 102%, 103%, 104%, 105%, 106%, 107%, 108%, 109%, or at least 110% thereof. Even more preferably, the value of the parameter, such as residual activity or $T_d$, of the protease of the invention is at least 120%, 130%, 140%, 150%, 160%, 170%, 180%, or at least 190% of the value for the protease of SEQ ID NO: 5.

In still further particular embodiments, the thermostable protease of the invention has a melting temperature, $T_m$ (or a denaturation temperature, $T_d$), as determined using Differential Scanning calorimetry (DSC) as described in example 10 (i.e. in 20 mM sodium acetate, pH 4.0), of at least 50° C. In still further particular embodiments, the $T_m$ is at least 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or at least 100° C.

Steam Stability

Steam stability may be determined as described in Example 7 by determining the residual activity of protease molecules after steam treatment at 85° C. or 90° C. for a short time.

Pelleting Stability

Pelleting stability may be determined as described in Example 8 by using enzyme granulate pre-mixed with feed. From the mixer the feed is conditioned with steam to 95° C. After conditioning the feed is pressed to pellets and the residual activity determined.

Sources of Polypeptides Having Protease Activity

A polypeptide having protease activity and to be used according to the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a bacterial polypeptide. For example, the polypeptide may be a polypeptide having protease activity from a gram-positive bacterium within a phylum such Actinobacteria or from a gram-negative bacterium within a phylum such as Proteobacteria.

In one aspect, the polypeptide is a protease from a bacterium of the class Actinobacteria, such as from the order Actinomycetales, or from the suborder Pseudonocardineae, or from the family Pseudonocardiaceae, or from the genus *Saccharopolyspora*, or from the species *Saccharopolyspora erythraea*.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these taxa are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) using the above-mentioned probes. Techniques for isolating microorganisms from natural habitats are well known in the art. The polynucleotide encoding the polypeptide may then be obtained by similarly screening a genomic or cDNA library of another microorganism or mixed DNA sample. Once a polynucleotide encoding a polypeptide has been detected with the probe(s), the polynucleotide can be isolated or cloned by utilizing techniques that are well known to those of ordinary skill in the art (see, e.g., Sambrook et al., 1989, supra).

Polynucleotides

The present invention also relates to isolated polynucleotides encoding a polypeptide of the present invention and used for recombinant production of the polypeptide.

The techniques used to isolate or clone a polynucleotide encoding a polypeptide are known in the art and include isolation from genomic DNA, preparation from cDNA, or a combination thereof. The cloning of the polynucleotides from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Saccharopolyspora*, or another or related organism from the Actinomycetales and thus, for example, may be an allelic or species variant of the polypeptide encoding region of the polynucleotide.

The present invention also relates to isolated polynucleotides comprising or consisting of polynucleotides having a degree of sequence identity to the mature polypeptide coding sequence of SEQ ID NO: 1 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, with the proviso that it is not 100% identical to the mature polypeptide coding sequence of SEQ ID NO: 1, and which encode a polypeptide having protease activity.

The present invention further relates to isolated polynucleotides comprising or consisting of polynucleotides having a degree of sequence identity to the mature polypeptide coding sequence of SEQ ID NO: 3 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which encode a polypeptide having protease activity.

Modification of a polynucleotide encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variant may be constructed on the basis of the polynucleotide presented as the mature polypeptide coding sequence of SEQ ID NO: 1 or SEQ ID NO: 3, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

The present invention also relates to isolated polynucleotides encoding polypeptides of the present invention, which hybridize under high stringency conditions, or very high stringency conditions with (i) the mature polypeptide coding sequence of SEQ ID NO: 1, (ii) the mature polypeptide coding sequence of SEQ ID NO: 3, (iii) the genomic DNA sequence comprising the mature polypeptide coding sequence of SEQ ID NO: 1, (iv) the genomic DNA sequence comprising the mature polypeptide coding sequence of SEQ ID NO: 3, or (v) the full-length complementary strand of (i), (ii), (iii), or (iv); or allelic variants and subsequences thereof (Sambrook et al., 1989, supra), as defined herein.

In one aspect, the polynucleotide comprises or consists of SEQ ID NO: 3, the mature polypeptide coding sequence of SEQ ID NO: 3, a subsequence of SEQ ID NO: 1 that encodes a fragment of SEQ ID NO: 2, SEQ ID NO: 4 or SEQ ID NO: 5 having protease activity, or a subsequence of SEQ ID NO: 3 that encodes a fragment of SEQ ID NO: 2, SEQ ID NO: 4 or SEQ ID NO: 5 having protease activity, such as the polynucleotide of nucleotides 550 to 1119 of SEQ ID NO: 3.

Nucleic Acid Constructs

The present invention also relates to nucleic acid constructs comprising a polynucleotide of the present invention operably linked to one or more (several) control sequences that direct the expression of the coding sequence in a suitable host cell under conditions compatible with the control sequences.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter sequence, a polynucleotide that is recognized by a host cell for expression of a polynucleotide encoding a polypeptide of the present invention. The promoter sequence contains transcriptional control sequences that mediate the expression of the polypeptide. The promoter may be any polynucleotide that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *E. coli* lac operon, *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American*, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dania (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV,

*Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter including a gene encoding a neutral alpha-amylase in Aspergilli in which the untranslated leader has been replaced by an untranslated leader from a gene encoding triose phosphate isomerase in Aspergilli; non-limiting examples include modified promoters including the gene encoding neutral alpha-amylase in *Aspergillus niger* in which the untranslated leader has been replaced by an untranslated leader from the gene encoding triose phosphate isomerase in *Aspergillus nidulans* or *Aspergillus oryzae*); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, which is recognized by a host cell to terminate transcription. The terminator sequence is operably linked to the 3'-terminus of the polynucleotide encoding the polypeptide. Any terminator that is functional in the host cell of choice may be used in the present invention.

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, when transcribed is a nontranslated region of an mRNA that is important for translation by the host cell. The leader sequence is operably linked to the 5'-terminus of the polynucleotide encoding the polypeptide. Any leader sequence that is functional in the host cell of choice may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell of choice may be used.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Mol. Cellular. Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present at the N-terminus of a polypeptide, the propeptide sequence is positioned next to the N-terminus of a polypeptide and the signal peptide sequence is positioned next to the N-terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more (several) convenient restriction sites to allow for insertion or substitution of the polynucleotide encoding the polypeptide at such sites. Alternatively, the polynucleotide may be expressed by inserting the polynucleotide or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers that confer antibiotic resistance such as ampicillin, chloramphenicol, kanamycin, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more (several) control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any gram-positive or gram-negative bacterium. Gram-positive bacteria include, but are not limited to, *Bacillus, Brevibacillus, Clostridium, Geobacillus, Lactobacillus, Lactococcus, Paenibacillus*, and *Streptomyces*. Gram-negative bacteria include, but are not limited to *E. coli*, and *Pseudomonas*.

The bacterial host cell may be any Bacillales cell including, but not limited to *Bacillus amyloliquefaciens, Brevibacillus brevis, Bacillus circulans, Bacillus clausii, Bacillus coagulans, Bacillus lentus, Bacillus licheniformis, Geobacillus stearothermophilus, Bacillus subtilis*, and *Bacillus thuringiensis* cells. A specifically preferred host cell is a *Bacillus lentus* cell.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may, for instance, be effected by protoplast transformation (see, e.g., Chang and Cohen, 1979, *Mol. Gen. Genet.* 168: 111-115), by using competent cells (see, e.g., Young and Spizizen, 1961, *J. Bacteriol.* 81: 823-829, or Dubnau and Davidoff-Abelson, 1971, *J. Mol. Biol.* 56: 209-221), by electroporation (see, e.g., Shigekawa and Dower, 1988, *Biotechniques* 6: 742-751), or by conjugation (see, e.g., Koehler and Thorne, 1987, *J. Bacteriol.* 169: 5271-5278). The introduction of DNA into an *E. coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol. (Praha)* 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios* 68: 189-207, by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series No. 9*, 1980).

The yeast host cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia*

*terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023 and Yelton et al., 1984, *Proc. Natl. Acad. Sci. USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising: (a) cultivating a cell, which in its wild-type form produces the polypeptide, under conditions conducive for production of the polypeptide; and (b) recovering the polypeptide. In one aspect, the cell is of the genus *Saccharopolyspora*. In a more preferred aspect, the cell is a *Saccharopolyspora erythraea* cell.

Chromosomal DNA of *Saccharopolyspora erythraea* can be isolated as indicated in Oliynyk et al.; Complete genome sequence of the erythromycin-producing bacterium *Saccharopolyspora erythraea* NRRL23338. Nat Biotechnol 25:447-453 (2007). This DNA can be used for the recombinant production of a protease to be used according to the invention.

The present invention also relates to methods of producing a polypeptide of the present invention, comprising: (a) cultivating a recombinant host cell of the present invention under conditions conducive for production of the polypeptide; and (b) recovering the polypeptide.

The host cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

More details are provided in the Sections above and in the Section on "Nucleic Acid Constructs, Expression Vectors, Recombinant Host Cells, and Methods for Production of Proteases" below.

The polypeptide may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

In an alternative aspect, the polypeptide is not recovered, but rather a host cell of the present invention expressing a polypeptide is used as a source of the polypeptide.

Plants

The present invention also relates to plants, e.g., a transgenic plant, plant part, or plant cell, comprising an isolated polynucleotide of the present invention so as to express and produce the polypeptide in recoverable quantities. The polypeptide may be recovered from the plant or plant part. Alternatively, the plant or plant part containing the polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seeds coats.

Also included within the scope of the present invention are the progeny of such plants, plant parts, and plant cells.

The transgenic plant or plant cell expressing a polypeptide may be constructed in accordance with methods known in the art. In short, the plant or plant cell is constructed by incorporating one or more (several) expression constructs encoding a polypeptide into the plant host genome or chloroplast genome and propagating the resulting modified plant or plant cell into a transgenic plant or plant cell.

The expression construct is conveniently a nucleic acid construct that comprises a polynucleotide encoding a polypeptide operably linked with appropriate regulatory sequences required for expression of the polynucleotide in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide is desired to be expressed. For instance, the expression of the gene encoding a polypeptide may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, and the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the chlorella virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide in the plant. For instance, the promoter enhancer element may be an intron that is placed between the promoter and the polynucleotide encoding a polypeptide. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Mol. Biol.* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods for use in accordance with the present disclosure include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct prepared according to the present invention, transgenic plants may be made by crossing a plant having the construct to a second plant lacking the construct. For example, a construct encoding a polypeptide can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention, or a portion of a DNA construct prepared in accordance with the present invention. Crossing results in the introduction of a transgene into a plant line by cross pollinating a starting line with a donor plant line. Non-limiting examples of such steps are further articulated in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide of the present invention comprising: (a) cultivating a transgenic plant or a plant cell comprising a polynucleotide encoding the polypeptide under conditions conducive for production of the polypeptide; and (b) recovering the polypeptide.

Compositions

The present invention also relates to compositions comprising a protease of the present invention. Preferably, the compositions are enriched in such a protease. The term "enriched" indicates that the protease activity of the composition has been increased, e.g., with an enrichment factor of at least 1.1.

The composition may comprise a protease of the present invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by microorganisms such as bacteria or fungi or by plants or by animals. The compositions may be prepared in accordance with methods known in the art and may be in the form of a liquid or a dry composition. For instance, the composition may be in the form of a granulate or a microgranulate. The protease may be stabilized in accordance with methods known in the art.

Uses

The present invention is directed to methods for using the polypeptides having protease activity, or compositions thereof.

Animal Feed

The present invention is directed to methods for using the proteases having protease activity in animal feed, as well as to feed compositions and feed additives comprising the proteases of the invention.

The term animal includes all animals, including human beings. Examples of animals are non-ruminants, and ruminants. Ruminant animals include, for example, animals such as sheep, goats, and cattle, e.g. beef cattle, cows, and young calves. In a particular embodiment, the animal is a non-ruminant animal. Non-ruminant animals include mono-gastric animals, e.g. pigs or swine (including, but not limited to, piglets, growing pigs, and sows); poultry such as turkeys, ducks and chicken (including but not limited to broiler chicks, layers); horses (including but not limited to hotbloods, coldbloods and warm bloods), young calves; and fish (including but not limited to salmon, trout, tilapia, catfish and carps; and crustaceans (including but not limited to shrimps and prawns).

The term feed or feed composition means any compound, preparation, mixture, or composition suitable for, or intended for intake by an animal.

In the use according to the invention the protease can be fed to the animal before, after, or simultaneously with the diet. The latter is preferred.

In a particular embodiment, the protease, in the form in which it is added to the feed, or when being included in a feed additive, is well-defined. Well-defined means that the protease preparation is at least 50% pure as determined by Size-exclusion chromatography (see Example 12 of WO 01/58275). In other particular embodiments the protease preparation is at least 60, 70, 80, 85, 88, 90, 92, 94, or at least 95% pure as determined by this method.

A well-defined protease preparation is advantageous. For instance, it is much easier to dose correctly to the feed a protease that is essentially free from interfering or contaminating other proteases. The term dose correctly refers in particular to the objective of obtaining consistent and constant results, and the capability of optimising dosage based upon the desired effect.

For the use in animal feed, however, the protease need not be that pure; it may e.g. include other enzymes, in which case it could be termed a protease preparation.

The protease preparation can be (a) added directly to the feed (or used directly in a protein treatment process), or (b) it can be used in the production of one or more intermediate compositions such as feed additives or premixes that is subsequently added to the feed (or used in a treatment process). The degree of purity described above refers to the purity of the original protease preparation, whether used according to (a) or (b) above.

Protease preparations with purities of this order of magnitude are in particular obtainable using recombinant methods of production, whereas they are not so easily obtained and also subject to a much higher batch-to-batch variation when the protease is produced by traditional fermentation methods.

Such protease preparation may of course be mixed with other enzymes.

The protein may be an animal protein, such as meat and bone meal, feather meal, and/or fish meal; or it may be a vegetable protein.

The term vegetable proteins as used herein refers to any compound, composition, preparation or mixture that includes at least one protein derived from or originating from a vegetable, including modified proteins and protein-derivatives. In particular embodiments, the protein content of the vegetable proteins is at least 10, 20, 30, 40, 50, or 60% (w/w).

Vegetable proteins may be derived from vegetable protein sources, such as legumes and cereals, for example materials from plants of the families Fabaceae (Leguminosae), Cruciferaceae, Chenopodiaceae, and Poaceae, such as soy bean meal, lupin meal and rapeseed meal.

In a particular embodiment, the vegetable protein source is material from one or more plants of the family Fabaceae, e.g. soybean, lupine, pea, or bean.

In another particular embodiment, the vegetable protein source is material from one or more plants of the family Chenopodiaceae, e.g. beet, sugar beet, spinach or quinoa.

Other examples of vegetable protein sources are rapeseed, sunflower seed, cotton seed, and cabbage.

Soybean is a preferred vegetable protein source.

Other examples of vegetable protein sources are cereals such as barley, wheat, rye, oat, maize (corn), rice, triticale, and sorghum.

In a particular embodiment of a treatment process the protease(s) in question is affecting (or acting on, or exerting its hydrolyzing or degrading influence on) the proteins, such as vegetable proteins or protein sources. To achieve this, the protein or protein source is typically suspended in a solvent, eg an aqueous solvent such as water, and the pH and temperature values are adjusted paying due regard to the characteristics of the enzyme in question. For example, the treatment may take place at a pH-value at which the activity of the actual protease is at least 5%, 10%, 20%, 30%, 40%, 50%, 60%, 70%, 80%, or at least 90%. Likewise, for example, the treatment may take place at a temperature at which the activity of the actual protease is at least 5%, 10%, 20%, 30%, 40%, 50%, 60%, 70%, 80%, or at least 90%. The above percentage activity indications are relative to the maximum activities. The enzymatic reaction is continued until the desired result is achieved, following which it may or may not be stopped by inactivating the enzyme, e.g. by a heat-treatment step.

In another particular embodiment of a treatment process of the invention, the protease action is sustained, meaning e.g. that the protease is added to the proteins, but its hydrolysing influence is so to speak not switched on until later when desired, once suitable hydrolysing conditions are established, or once any enzyme inhibitors are inactivated, or whatever other means could have been applied to postpone the action of the enzyme.

In one embodiment the treatment is a pre-treatment of animal feed or proteins for use in animal feed, i.e. the proteins are hydrolysed before intake.

The term improving the nutritional value of an animal feed means improving the availability of nutrients in the feed. In this invention improving the nutritional values refers in particular to improving the availability of the protein fraction of the feed, thereby leading to increased protein extraction, higher protein yields, and/or improved protein utilization. When the nutritional value of the feed is increased, the protein and/or amino acid digestibility is increased and the growth rate and/or weight gain and/or feed conversion (i.e. the weight of ingested feed relative to weight gain) of the animal might be improved.

The protease can be added to the feed in any form, be it as a relatively pure protease or in admixture with other components intended for addition to animal feed, i.e. in the form of animal feed additives, such as the so-called premixes for animal feed.

In a further aspect the present invention relates to compositions for use in animal feed, such as animal feed, and animal feed additives, e.g. premixes.

Apart from the protease of the invention, the animal feed additives of the invention contain at least one fat-soluble vitamin, and/or at least one water soluble vitamin, and/or at least one trace mineral, and/or at least one macro mineral.

Further, optional, feed-additive ingredients are colouring agents, e.g. carotenoids such as beta-carotene, astaxanthin, and lutein; stabilisers; growth improving additives and aroma compounds/flavorings, e.g. creosol, anethol, deca-, undeca- and/or dodeca-lactones, ionones, irone, gingerol, piperidine, propylidene phatalide, butylidene phatalide, capsaicin and/or tannin; antimicrobial peptides; polyunsaturated fatty acids (PUFAs); reactive oxygen generating species; also, a support may be used that may contain, for example, 40-50% by weight of wood fibres, 8-10% by weight of stearine, 4-5% by weight of curcuma powder, 4-58% by weight of rosemary powder, 22-28% by weight of limestone, 1-3% by weight of a gum, such as gum arabic, 5-50% by weight of sugar and/or starch and 5-15% by weight of water.

A feed or a feed additive of the invention may also comprise at least one other enzyme selected from amongst phytase (EC 3.1.3.8 or 3.1.3.26); xylanase (EC 3.2.1.8); galactanase (EC 3.2.1.89); alpha-galactosidase (EC 3.2.1.22); further protease (EC 3.4), phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); amylase such as, for example, alpha-amylase (EC 3.2.1.1); and/or beta-glucanase (EC 3.2.1.4 or EC 3.2.1.6).

In a particular embodiment these other enzymes are well-defined (as defined above for protease preparations).

Examples of antimicrobial peptides (AMP's) are CAP18, Leucocin A, Tritrpticin, Protegrin-1, Thanatin, Defensin, Lactoferrin, Lactoferricin, and Ovispirin such as Novispirin (Robert Lehrer, 2000), Plectasins, and Statins, including the compounds and polypeptides disclosed in WO 03/044049 and WO 03/048148, as well as variants or fragments of the above that retain antimicrobial activity.

Examples of antifungal polypeptides (AFP's) are the *Aspergillus giganteus*, and *Aspergillus niger* peptides, as well as variants and fragments thereof which retain antifungal activity, as disclosed in WO 94/01459 and WO 02/090384.

Examples of polyunsaturated fatty acids are C18, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and enzymes such as an oxidase, an oxygenase or a synthetase.

Usally fat- and water-soluble vitamins, as well as trace minerals form part of a so-called premix intended for addition to the feed, whereas macro minerals are usually separately added to the feed. Either of these composition types, when enriched with a protease of the invention, is an animal feed additive of the invention.

In a particular embodiment, the animal feed additive of the invention is intended for being included (or prescribed as having to be included) in animal diets or feed at levels of 0.01 to 10.0%; more particularly 0.05 to 5.0%; or 0.2 to 1.0% (% meaning g additive per 100 g feed). This is so in particular for premixes.

The following are non-exclusive lists of examples of these components:

Examples of fat-soluble vitamins are vitamin A, vitamin D3, vitamin E, and vitamin K, e.g. vitamin K3.

Examples of water-soluble vitamins are vitamin B12, biotin and choline, vitamin B1, vitamin B2, vitamin B6, niacin, folic acid and panthothenate, e.g. Ca-D-panthothenate.

Examples of trace minerals are manganese, zinc, iron, copper, iodine, selenium, and cobalt.

Examples of macro minerals are calcium, phosphorus and sodium.

The nutritional requirements of these components (exemplified with poultry and piglets/pigs) are listed in Table A of WO 01/58275. Nutritional requirement means that these components should be provided in the diet in the concentrations indicated.

In the alternative, the animal feed additive of the invention comprises at least one of the individual components specified in Table A of WO 01/58275. At least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A.

In a still further embodiment, the animal feed additive of the invention comprises at least one of the below vitamins, preferably to provide an in-feed-concentration within the ranges specified in the below Table 1 (for piglet diets, and broiler diets, respectively).

TABLE 1

Typical vitamin recommendations

| Vitamin | Piglet diet | Broiler diet |
|---|---|---|
| Vitamin A | 10,000-15,000 IU/kg feed | 8-12,500 IU/kg feed |
| Vitamin D3 | 1800-2000 IU/kg feed | 3000-5000 IU/kg feed |

TABLE 1-continued

Typical vitamin recommendations

| Vitamin | Piglet diet | Broiler diet |
|---|---|---|
| Vitamin E | 60-100 mg/kg feed | 150-240 mg/kg feed |
| Vitamin K3 | 2-4 mg/kg feed | 2-4 mg/kg feed |
| Vitamin B1 | 2-4 mg/kg feed | 2-3 mg/kg feed |
| Vitamin B2 | 6-10 mg/kg feed | 7-9 mg/kg feed |
| Vitamin B6 | 4-8 mg/kg feed | 3-6 mg/kg feed |
| Vitamin B12 | 0.03-0.05 mg/kg feed | 0.015-0.04 mg/kg feed |
| Niacin (Vitamin B3) | 30-50 mg/kg feed | 50-80 mg/kg feed |
| Pantothenic acid | 20-40 mg/kg feed | 10-18 mg/kg feed |
| Folic acid | 1-2 mg/kg feed | 1-2 mg/kg feed |
| Biotin | 0.15-0.4 mg/kg feed | 0.15-0.3 mg/kg feed |
| Choline chloride | 200-400 mg/kg feed | 300-600 mg/kg feed |

The present invention also relates to animal feed compositions. Animal feed compositions or diets have a relatively high content of protein. Poultry and pig diets can be characterised as indicated in Table B of WO 01/58275, columns 2-3. Fish diets can be characterised as indicated in column 4 of this Table B. Furthermore such fish diets usually have a crude fat content of 200-310 g/kg.

WO 01/58275 corresponds to U.S. Ser. No. 09/779,334 which is hereby incorporated by reference.

An animal feed composition according to the invention has a crude protein content of 50-800 g/kg, and furthermore comprises at least one protease as claimed herein.

Furthermore, or in the alternative (to the crude protein content indicated above), the animal feed composition of the invention has a content of metabolisable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In particular embodiments, the content of metabolisable energy, crude protein, calcium, phosphorus, methionine, methionine plus cysteine, and/or lysine is within any one of ranges 2, 3, 4 or 5 in Table B of WO 01/58275 (R. 2-5).

Crude protein is calculated as nitrogen (N) multiplied by a factor 6.25, i.e. Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington D.C.).

Metabolisable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 DA Beekbergen, The Netherlands. Grafisch bedrijf Ponsen & Iooijen by, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In a particular embodiment, the animal feed composition of the invention contains at least one vegetable protein as defined above.

The animal feed composition of the invention may also contain animal protein, such as Meat and Bone Meal, Feather meal, and/or Fish Meal, typically in an amount of 0-25%. The animal feed composition of the invention may also comprise Dried Destillers Grains with Solubles (DDGS), typically in amounts of 0-30%.

In still further particular embodiments, the animal feed composition of the invention contains 0-80% maize; and/or 0-80% sorghum; and/or 0-70% wheat; and/or 0-70% Barley; and/or 0-30% oats; and/or 0-40% soybean meal; and/or 0-25% fish meal; and/or 0-25% meat and bone meal; and/or 0-20% whey.

Animal diets can e.g. be manufactured as mash feed (non pelleted) or pelleted feed. Typically, the milled feed-stuffs are mixed and sufficient amounts of essential vitamins and minerals are added according to the specifications for the species in question. Enzymes can be added as solid or liquid enzyme formulations. For example, for mash feed a solid or liquid enzyme formulation may be added before or during the ingredient mixing step. For pelleted feed the (liquid or solid) protease/enzyme preparation may also be added before or during the feed ingredient step. Typically a liquid protease/enzyme preparation is added after the pelleting step. The enzyme may also be incorporated in a feed additive or premix.

The final enzyme concentration in the diet is within the range of 0.01-200 mg enzyme protein per kg diet, for example in the range of 0.5-25 mg enzyme protein per kg animal diet.

The protease should of course be applied in an effective amount, i.e. in an amount adequate for improving hydrolysis, digestibility, and/or improving nutritional value of feed. It is at present contemplated that the enzyme is administered in one or more of the following amounts (dosage ranges): 0.01-200; 0.01-100; 0.5-100; 1-50; 5-100; 10-100; 0.05-50; or 0.10-10—all these ranges being in mg protease protein per kg feed (ppm).

For determining mg protease protein per kg feed, the protease is purified from the feed composition, and the specific activity of the purified protease is determined using a relevant assay (see under protease activity, substrates, and assays). The protease activity of the feed composition as such is also determined using the same assay, and on the basis of these two determinations, the dosage in mg protease protein per kg feed is calculated.

The same principles apply for determining mg protease protein in feed additives. Of course, if a sample is available of the protease used for preparing the feed additive or the feed, the specific activity is determined from this sample (no need to purify the protease from the feed composition or the additive).

Detergent Compositions

In one embodiment, the invention is directed to detergent compositions comprising an enzyme of the present invention in combination with one or more additional cleaning composition components. The choice of additional components is within the skill of the artisan and includes conventional ingredients, including the exemplary non-limiting components set forth below.

The choice of components may include, for textile care, the consideration of the type of textile to be cleaned, the type and/or degree of soiling, the temperature at which cleaning is to take place, and the formulation of the detergent product. Although components mentioned below are categorized by general header according to a particular functionality, this is not to be construed as a limitation since the component may have one or more additional functionalities which the skilled artisan will appreciate.

The detergent composition may be suitable for the laundring of textiles such as e.g. fabrics, cloths or linen, or for cleaning hard surfaces such as e.g. floors, tables, or dish wash.

Enzyme Amounts in Detergent Compositions

In one embodiment of the present invention, the a polypeptide of the present invention may be added to a detergent composition in an amount corresponding to 0.0001-200 mg of enzyme protein, such as 0.0005-100 mg of enzyme protein, preferably 0.001-30 mg of enzyme protein, more preferably 0.005-8 mg of enzyme protein, even more preferably 0.01-2 mg of enzyme protein per liter of wash liquor.

A composition for use in automatic dishwash (ADW), for example, may include 0.0001%-50%, such as 0.001%-20%, such as 0.01%-10%, such as 0.05-5% of enzyme protein by weight of the composition.

A composition for use in laundry granulation, for example, may include 0.0001%-50%, such as 0.001%-20%, such as 0.01%-10%, such as 0.05%-5% of enzyme protein by weight of the composition.

A composition for use in laundry liquid, for example, may include 0.0001%-10%, such as 0.001-7%, such as 0.1%-5% of enzyme protein by weight of the composition.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, for example, WO92/19709 and WO92/19708.

In certain markets different wash conditions and, as such, different types of detergents are used. This is disclosed in e.g. EP 1 025 240. For example, In Asia (Japan) a low detergent concentration system is used, while the United States uses a medium detergent concentration system, and Europe uses a high detergent concentration system.

A low detergent concentration system includes detergents where less than about 800 ppm of detergent components are present in the wash water. Japanese detergents are typically considered low detergent concentration system as they have approximately 667 ppm of detergent components present in the wash water.

A medium detergent concentration includes detergents where between about 800 ppm and about 2000 ppm of detergent components are present in the wash water. North American detergents are generally considered to be medium detergent concentration systems as they have approximately 975 ppm of detergent components present in the wash water.

A high detergent concentration system includes detergents where greater than about 2000 ppm of detergent components are present in the wash water. European detergents are generally considered to be high detergent concentration systems as they have approximately 4500-5000 ppm of detergent components in the wash water.

Latin American detergents are generally high suds phosphate builder detergents and the range of detergents used in Latin America can fall in both the medium and high detergent concentrations as they range from 1500 ppm to 6000 ppm of detergent components in the wash water. Such detergent compositions are all embodiments of the invention.

A polypeptide of the present invention may also be incorporated in the detergent formulations disclosed in WO97/07202, which is hereby incorporated by reference.

Surfactants

The detergent composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 0.1% to 60% by weight, such as about 1% to about 40%, or about 3% to about 20%, or about 3% to about 10%. The surfactant(s) is chosen based on the desired cleaning application, and includes any conventional surfactant(s) known in the art. Any surfactant known in the art for use in detergents may be utilized.

When included therein the detergent will usually contain from about 1% to about 40% by weight, such as from about 5% to about 30%, including from about 5% to about 15%, or from about 20% to about 25% of an anionic surfactant. Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or soap, and combinations thereof.

When included therein the detergent will usually contain from about 0% to about 10% by weight of a cationic surfactant. Non-limiting examples of cationic surfactants include alklydimethylethanolamine quat (ADMEAQ), cetyltrimethylammonium bromide (CTAB), dimethyldistearylammonium chloride (DSDMAC), and alkylbenzyldimethylammonium, alkyl quaternary ammonium compounds, alkoxylated quaternary ammonium (AQA) compounds, and combinations thereof.

When included therein the detergent will usually contain from about 0.2% to about 40% by weight of a non-ionic surfactant, for example from about 0.5% to about 30%, in particular from about 1% to about 20%, from about 3% to about 10%, such as from about 3% to about 5%, or from about 8% to about 12%. Non-limiting examples of non-ionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxy alkyl fatty acid amides, or N-acyl N-alkyl derivatives of glucosamine (glucamides, GA, or fatty acid glucamide, FAGA), as well as products available under the trade names SPAN and TWEEN, and combinations thereof.

When included therein the detergent will usually contain from about 0% to about 10% by weight of a semipolar surfactant. Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl)amine oxide, fatty acid alkanolamides and ethoxylated fatty acid alkanolamides, and combinations thereof.

When included therein the detergent will usually contain from about 0% to about 10% by weight of a zwitterionic surfactant. Non-limiting examples of zwitterionic surfactants include betaine, alkyldimethylbetaine, sulfobetaine, and combinations thereof.

Hydrotropes

A hydrotrope is a compound that solubilises hydrophobic compounds in aqueous solutions (or oppositely, polar substances in a non-polar environment). Typically, hydrotropes have both hydrophilic and a hydrophobic character (so-called amphiphilic properties as known from surfactants); however the molecular structure of hydrotropes generally do not favor spontaneous self-aggregation, see e.g. review by Hodgdon and Kaler (2007), Current Opinion in Colloid & Interface Science 12: 121-128. Hydrotropes do not display a critical concentration above which self-aggregation occurs as found for surfactants and lipids forming miceller, lamellar or other well defined meso-phases. Instead, many hydrotropes show a continuous-type aggregation process where the sizes of aggregates grow as concentration increases. However, many hydrotropes alter the phase behavior, stability, and colloidal properties of systems containing substances of polar and non-polar character, including mixtures of water, oil, surfactants, and polymers. Hydrotropes are classically used across industries from pharma, personal care, food, to technical applications. Use of hydrotropes in detergent compositions allow for example more concentrated formulations of surfactants (as in the process of compacting liquid detergents by removing water) without inducing undesired phenomena such as phase separation or high viscosity.

The detergent may contain 0-5% by weight, such as about 0.5 to about 5%, or about 3% to about 5%, of a hydrotrope. Any hydrotrope known in the art for use in detergents may be utilized. Non-limiting examples of hydrotropes include sodium benzene sulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Builders and Co-Builders

The detergent composition may contain about 0-65% by weight, such as about 5% to about 45% of a detergent builder or co-builder, or a mixture thereof. In a dish wash detergent, the level of builder is typically 40-65%, particularly 50-65%. The builder and/or co-builder may particularly be a chelating agent that forms water-soluble complexes with Ca and Mg. Any builder and/or co-builder known in the art for use in laundry detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), diethanolamine (DEA, also known as iminodiethanol), triethanolamine (TEA, also known as 2,2',2"-nitrilotriethanol), and carboxymethyl inulin (CMI), and combinations thereof.

The detergent composition may also contain 0-20% by weight, such as about 5% to about 10%, of a detergent co-builder, or a mixture thereof. The detergent composition may include include a co-builder alone, or in combination with a builder, for example a zeolite builder. Non-limiting examples of co-builders include homopolymers of polyacrylates or copolymers thereof, such as poly(acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diphosphonic acid (HEDP), ethylenediaminetetra-(methylenephosphonic acid) (EDTMPA), diethylenetriaminepentakis(methylenephosphonic acid) (DTPMPA or DTMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl)-aspartic acid (SMAS), N-(2-sulfoethyl)-aspartic acid (SEAS), N-(2-sulfomethyl)-glutamic acid (SMGL), N-(2-sulfoethyl)-glutamic acid (SEGL), N-methyliminodiacetic acid (MIDA), α-alanine-N,N-diacetic acid (α-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA), N-(2-hydroxyethyl)-ethylidenediamine-N,N',N'-triacetate (HEDTA), diethanolglycine (DEG), diethylenetriamine penta(methylenephosphonic acid) (DTPMP), aminotris(methylenephosphonic acid) (ATMP), and combinations and salts thereof. Further exemplary builders and/or co-builders are described in, e.g., WO 09/102,854, U.S. Pat. No. 5,977,053

Bleaching Systems

The detergent may contain 0-50% by weight, such as about 0.1% to about 25%, of a bleaching system. Any bleaching system known in the art for use in laundry detergents may be utilized. Suitable bleaching system components include bleaching catalysts, photobleaches, bleach activators, sources of hydrogen peroxide such as sodium percarbonate and sodium perborates, preformed peracids and mixtures thereof. Suitable preformed peracids include, but are not limited to, peroxycarboxylic acids and salts, percarbonic acids and salts, perimidic acids and salts, peroxymonosulfuric acids and salts, for example, Oxone (R), and mixtures thereof. Non-limiting examples of bleaching systems include peroxide-based bleaching systems, which may comprise, for example, an inorganic salt, including alkali metal salts such as sodium salts of perborate (usually mono- or tetra-hydrate), percarbonate, persulfate, perphosphate, persilicate salts, in combination with a peracid-forming bleach activator. The term bleach activator is meant herein as a compound which reacts with peroxygen bleach like hydrogen peroxide to form a peracid. The peracid thus formed constitutes the activated bleach. Suitable bleach activators to be used herein include those belonging to the class of esters amides, imides or anhydrides. Suitable examples are tetracetylethylene diamine (TAED), sodium 4-[(3,5,5-trimethylhexanoyl)oxy]benzene sulfonate (ISONOBS), diperoxy dodecanoic acid, 4-(dodecanoyloxy) benzenesulfonate (LOBS), 4-(decanoyloxy)benzenesulfonate, 4-(decanoyloxy)benzoate (DOBS), 4-(nonanoyloxy)-benzenesulfonate (NOBS), and/or those disclosed in WO98/17767. A particular family of bleach activators of interest was disclosed in EP624154 and particularly preferred in that family is acetyl triethyl citrate (ATC). ATC or a short chain triglyceride like triacetin has the advantage that it is environmental friendly as it eventually degrades into citric acid and alcohol. Furthermore acetyl triethyl citrate and triacetin has a good hydrolytical stability in the product upon storage and it is an efficient bleach activator. Finally ATC provides a good building capacity to the laundry additive. Alternatively, the bleaching system may comprise peroxyacids of, for example, the amide, imide, or sulfone type. The bleaching system may also comprise peracids such as 6-(phthalimido)peroxyhexanoic acid (PAP). The bleaching system may also include a bleach catalyst. In some embodiments the bleach component may be an organic catalyst selected from the group consisting of organic catalysts having the following formulae:

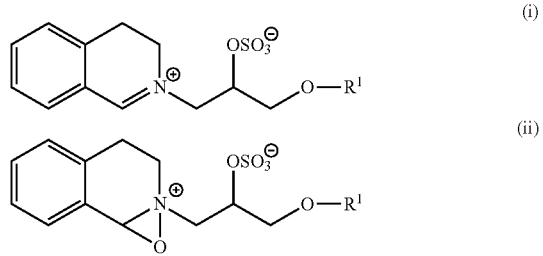

(iii) and mixtures thereof; wherein each $R^1$ is independently a branched alkyl group containing from 9 to 24 carbons or linear alkyl group containing from 11 to 24 carbons, preferably each $R^1$ is independently a branched alkyl group containing from 9 to 18 carbons or linear alkyl group containing from 11 to 18 carbons, more preferably each $R^1$ is independently selected from the group consisting of 2-propylheptyl, 2-butyloctyl, 2-pentylnonyl, 2-hexyldecyl, n-dodecyl, n-tetradecyl, n-hexadecyl, n-octadecyl, iso-nonyl, iso-decyl, iso-tridecyl and iso-pentadecyl. Other exemplary bleaching systems are described, e.g. in WO2007/087258, WO2007/087244, WO2007/087259 and WO2007/087242. Suitable photobleaches may for example be sulfonated zinc phthalocyanine Polymers The detergent may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or antifoaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly (ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly (oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated.

Fabric Hueing Agents

The detergent compositions of the present invention may also include fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO2005/03274, WO2005/03275, WO2005/03276 and EP1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g. WO 2007/087257 and WO2007/087243.

Additional Enzymes

The detergent additive as well as the detergent composition may comprise one or more additional enzymes such as a protease, lipase, cutinase, an amylase, carbohydrase, cellulase, pectinase, mannanase, arabinase, galactanase, xylanase, oxidase, e.g., a laccase, and/or peroxidase.

In general the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases:

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299.

Example of cellulases exhibiting endo-beta-1,4-glucanase activity (EC 3.2.1.4) are those having described in WO02/099091.

Other examples of cellulases include the family 45 cellulases described in WO96/29397, and especially variants thereof having substitution, insertion and/or deletion at one or more of the positions corresponding to the following positions in SEQ ID NO: 8 of WO 02/099091:2, 4, 7, 8, 10, 13, 15, 19, 20, 21, 25, 26, 29, 32, 33, 34, 35, 37, 40, 42, 42a, 43, 44, 48, 53, 54, 55, 58, 59, 63, 64, 65, 66, 67, 70, 72, 76, 79, 80, 82, 84, 86, 88, 90, 91, 93, 95, 95d, 95h, 95j, 97, 100, 101, 102, 103, 113, 114, 117, 119, 121, 133, 136, 137, 138, 139, 140a, 141, 143a, 145, 146, 147, 150e, 150j, 151, 152, 153, 154, 155, 156, 157, 158, 159, 160c, 160e, 160k, 161, 162, 164, 165, 168, 170, 171, 172, 173, 175, 176, 178, 181, 183, 184, 185, 186, 188, 191, 192, 195, 196, 200, and/or 20, preferably selected among P19A, G20K, Q44K, N48E, Q119H or Q146 R.

Commercially available cellulases include Celluzyme™, and Carezyme™ (Novozymes A/S), Clazinase™, and Puradax HA™ (Genencor International Inc.), and KAC-500 (B)™ (Kao Corporation).

Proteases:

The additional enzyme may be another protease or protease variant. The protease may be of animal, vegetable or microbial origin, including chemically or genetically modified mutants. Microbial origin is preferred. It may be an alkaline protease, such as a serine protease or a metalloprotease. A serine protease may for example be of the S1 family, such as trypsin, or the S8 family such as subtilisin. A metalloproteases protease may for example be a thermolysin from e.g. family M4, M5, M7 or M8.

The term "subtilases" refers to a sub-group of serine protease according to Siezen et al., Protein Engng. 4 (1991) 719-737 and Siezen et al. Protein Science 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family. In one aspect of the invention the protease may be a subtilase, such as a subtilisin or a variant hereof. Further the subtilases (and the serine proteases) are characterised by having two active site amino acid residues apart from the serine, namely a histidine and an aspartic acid residue.

Examples of subtilisins are those derived from Bacillus such as subtilisin lentus, Bacillus lentus, subtilisin Novo, subtilisin Carlsberg, Bacillus licheniformis, subtilisin BPN', subtilisin 309, subtilisin 147 and subtilisin 168 described in WO 89/06279 and protease PD138 (WO 93/18140). Additional serine protease examples are described in WO 98/020115, WO 01/44452, WO 01/58275, WO 01/58276, WO 03/006602 and WO 04/099401. An example of a subtilase variants may be those having mutations in any of the positions: 3, 4, 9, 15, 27, 36, 68, 76, 87, 95, 96, 97, 98, 99, 100, 101, 102, 103, 104, 106, 118, 120, 123, 128, 129, 130, 160, 167, 170, 194, 195, 199, 205, 217, 218, 222, 232, 235, 236, 245, 248, 252 and 274 using the BPN' numbering. More preferred the subtilase variants may comprise the mutations: S3T, V4I, S9R, A15T, K27R, *36D, V68A, N76D, N87S,R, *97E, A98S, S99G,D,A, S99AD, S101G, M,R S103A, V104I,Y,N, S106A, G118V,R, H120D,N, N123S, S128L, P129Q, S130A, G160D, Y167A, R170S, A194P, G195E, V199M, V205I, L217D, N218D, M222S, A232V, K235L, Q236H, Q245R, N252K, T274A (using BPN' numbering). A further preferred protease is the alkaline protease from Bacillus lentus DSM 5483, as described for example in WO 95/23221, and variants thereof which are described in WO 92/21760, WO 95/23221, EP 1921147 and EP 1921148.

Examples of trypsin-like proteases are trypsin (e.g. of porcine or bovine origin) and the Fusarium protease described in WO 89/06270 and WO 94/25583. Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235, and 274.

Examples of metalloproteases are the neutral metalloprotease as described in WO 07/044,993.

Preferred commercially available protease enzymes include Alcalase™, Coronase™, Duralase™, Durazym™, Esperase™, Everlase™, Kannase™, Liquanase™, Liquanase Ultra™, Ovozyme™, Polarzyme™, Primase™, Relase™, Savinase and Savinase Ultra™, (Novozymes A/S), Axapem™ (Gist-Brocases N.V.), BLAP and BLAP X (Henkel AG & Co. KGaA), Excellase™, FN2™, FN3™, FN4™, Maxaca™, Maxapem™, Maxatase™, Properase™, Purafast™, Purafect™, Purafect OxP™, Purafect Prime™ and Puramax™ (Genencor int.).

Lipases and Cutinases:

Suitable lipases and cutinases include those of bacterial or fungal origin. Chemically modified or protein engineered mutant enzymes are included. Examples include lipase from Thermomyces, e.g. from T. lanuginosus (previously named Humicola lanuginosa) as described in EP258068 and EP305216, cutinase from Humicola, e.g. H. insolens (WO96/13580), lipase from strains of Pseudomonas (some of these now renamed to Burkholderia), e.g. P. alcaligenes or P. pseudoalcaligenes (EP218272), P. cepacia (EP331376), P. sp. strain SD705 (WO95/06720 & WO96/27002), P. wisconsinensis (WO96/12012), GDSL-type Streptomyces lipases (WO10/065,455), cutinase from Magnaporthe grisea (WO10/107,560), cutinase from Pseudomonas mendocina (U.S. Pat. No. 5,389,536), lipase from Thermobifida fusca (WO11/084,412), Geobacillus stearothermophilus lipase (WO11/084,417), lipase from Bacillus subtilis (WO11/084,599), and lipase from Streptomyces griseus (WO11/150,157) and S. pristinaespiralis (WO12/137,147).

Further examples are lipases sometimes referred to as acyltransferases or perhydrolases, e.g. acyltransferases with homology to Candida antarctica lipase A (WO10/111,143), acyltransferase from Mycobacterium smegmatis (WO05/56782), perhydrolases from the CE 7 family (WO09/67279), and variants of the M. smegmatis perhydrolase in particular the S54V variant used in the commercial product Gentle Power Bleach from Huntsman Textile Effects Pte Ltd (WO10/100,028).

Other examples are lipase variants such as those described in EP407225, WO92/05249, WO94/01541, WO94/25578, WO95/14783, WO95/30744, WO95/35381, WO95/22615, WO96/00292, WO97/04079, WO97/07202, WO00/34450, WO00/60063, WO01/92502, WO07/87508 and WO09/109, 500.

Preferred commercial lipase products include Lipolase™, Lipex™; Lipolex™ and Lipoclean™ (Novozymes A/S), Lumafast (originally from Genencor) and Lipomax (originally from Gist-Brocades).

Amylases:

The amylase may be an alpha-amylase, a beta-amylase or a glucoamylase and may be of bacterial or fungal origin. Chemically modified or protein engineered mutants are included. Amylases include, for example, alpha-amylases obtained from Bacillus, e.g., a special strain of Bacillus licheniformis, described in more detail in GB 1,296,839.

Examples of amylases are those having SEQ ID NO: 3 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444 of SEQ ID NO: 3 in WO 95/10603.

Other amylases which can be used are amylases having SEQ ID NO: 6 in WO 02/010355 or variants thereof as well as hybrid alpha-amylase comprising residues 1-33 of the alpha-amylase derived from B. amyloliquefaciens shown in SEQ ID NO: 6 of WO 2006/066594 and residues 36-483 of the B. licheniformis alpha-amylase shown in SEQ ID NO: 4 of WO 2006/066594.

Further amylase examples are amylases having SEQ ID NO: 6 in WO 99/019467 or variants thereof and amylases having SEQ ID NO: 1, SEQ ID NO: 2 or SEQ ID NO: 7 of WO 96/023873 or variants thereof. Other amylases which can be used are amylases having SEQ ID NO: 2 of WO 08/153,815, SEQ ID NO: 10 in WO 01/66712 or variants thereof.

Additional amylases which can be used are amylases having SEQ ID NO: 2 of WO 09/061,380 or variants thereof and alpha-amylases having SEQ ID NO: 12 in WO01/66712 or a variant thereof.

Commercially available amylases are Duramyl™, Termamyl™, Fungamyl™, Stainzyme™, Stainzyme Plus™, Natalase™ and BAN™ (Novozymes A/S), Rapidase™ and Purastar™ (from Genencor International Inc.).

Peroxidases/Oxidases:

Suitable peroxidases/oxidases include those of plant, bacterial or fungal origin. Chemically modified or protein engineered mutants are included. Examples of useful peroxidases include peroxidases from Coprinus, e.g., from C. cinereus, and variants thereof as those described in WO 93/24618, WO 95/10602, and WO 98/15257.

Commercially available peroxidases include Guardzyme™ (Novozymes A/S).

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

Adjunct Materials

Any detergent components known in the art for use in laundry detergents may also be utilized. Other optional detergent components include anti-corrosion agents, anti-shrink agents, anti-soil redeposition agents, anti-wrinkling agents, bactericides, binders, corrosion inhibitors, disintegrants/disintegration agents, dyes, enzyme stabilizers (including boric acid, borates, CMC, and/or polyols such as propylene glycol), fabric conditioners including clays, fillers/processing aids, fluorescent whitening agents/optical brighteners, foam boosters, foam (suds) regulators, perfumes, soil-suspending agents, softeners, suds suppressors, tarnish inhibitors, and wicking agents, either alone or in combination. Any ingredient known in the art for use in laundry detergents may be utilized. The choice of such ingredients is well within the skill of the artisan.

Dispersants:

The detergent compositions of the present invention can also contain dispersants. In particular powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents:

The detergent compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent Whitening Agent:

The detergent compositions of the present invention will preferably also contain additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulphonic acid derivatives, diarylpyrazoline derivatives and bisphenyl-distyryl derivatives. Examples of the diaminostilbene-sulphonic acid derivative type of fluorescent whitening agents include the sodium salts of: 4,4'-bis-(2-diethanolamino-4-anilino-s-triazin-6-ylamino) stilbene-2,2'-disulphonate; 4,4'-bis-(2,4-dianilino-s-triazin-6-ylamino) stilbene-2,2'-disulphonate; 4,4'-bis-(2-anilino-4(N-methyl-N-2-hydroxy-ethylamino)-s-triazin-6-ylamino) stilbene-2,2'-disulphonate, 4,4'-bis-(4-phenyl-2,1,3-triazol-2-yl)stilbene-2,2'-disulphonate; 4,4'-bis-(2-anilino-4(1-methyl-2-hydroxy-ethylamino)-s-triazin-6-ylamino) stilbene-2,2'-disulphonate and 2-(stilbyl-4"-naptho-1.,2':4, 5)-1,2,3-trizole-2"-sulphonate. Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4 anilino-s-triazin-6-ylamino) stilbene disulphonate. Tinopal CBS is the disodium salt of 2,2'-bis-(phenyl-styryl)disulphonate. Also preferred are fluorescent whitening agents is the commercially available Parawhite KX, supplied by Paramount Minerals and Chemicals, Mumbai, India. Other fluorescers suitable for use in the invention include the 1-3-diaryl pyrazolines and the 7-alkylaminocoumarins. Suitable fluorescent brightener levels include lower levels of from about 0.01, from 0.05, from about 0.1 or even from about 0.2 wt % to upper levels of 0.5 or even 0.75 wt %.

Soil Release Polymers:

The detergent compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalate based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore random graft co-polymers are suitable soil release polymers Suitable graft co-polymers are described in more detail in WO 2007/138054, WO 2006/108856 and WO 2006/113314 (hereby incorporated by reference). Other soil release polymers are substituted polysaccharide structures especially substituted cellulosic structures such as modified cellulose deriviatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyethyl cellulose, hydroxylpropyl methyl cellulose, ester carboxy methyl cellulose, and mixtures thereof.

Anti-Redeposition Agents:

The detergent compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Other suitable adjunct materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Formulation of Detergent Products

The detergent composition of the invention may be in any convenient form, e.g., a bar, a homogenous tablet, a tablet having two or more layers, a pouch having one or more compartments, a regular or compact powder, a granule, a paste, a gel, or a regular, compact or concentrated liquid. There are a number of detergent formulation forms such as layers (same or different phases), pouches, as well as forms for machine dosing unit.

Pouches can be configured as single or multicompartments. It can be of any form, shape and material which is suitable for hold the composition, e.g. without allowing the release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxyprpyl methyl cellulose (HPMC). Preferably the level of polymer in the film for example PVA is at least about 60%. Preferred average molecular weight will typically be about 20,000 to about 150,000. Films can also be of blend compositions comprising hydrolytically degradable and water soluble polymer blends such as polylactide and polyvinyl alcohol (known under the Trade reference M8630 as sold by Chris Craft In. Prod. Of Gary, Ind., US) plus plasticisers like glycerol, ethylene glycerol, Propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids. Ref: (US2009/0011970 A1).

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent. A liquid or gel detergent may be non-aqueous.

Laundry Soap Bars

The enzymes of the invention may be added to laundry soap bars and used for hand washing laundry, fabrics and/or textiles. The term laundry soap bar includes laundry bars, soap bars, combo bars, syndet bars and detergent bars. The types of bar usually differ in the type of surfactant they contain, and the term laundry soap bar includes those containing soaps from fatty acids and/or synthetic soaps. The laundry soap bar has a physical form which is solid and not a liquid, gel or a powder at room temperature. The term solid is defined as a physical form which does not significantly change over time, i.e. if a solid object (e.g. laundry soap bar) is placed inside a container, the solid object does not change to fill the container it is placed in. The bar is a solid typically in bar form but can be in other solid shapes such as round or oval.

The laundry soap bar may contain one or more additional enzymes, protease inhibitors such as peptide aldehydes (or hydrosulfite adduct or hemiacetal adduct), boric acid, borate, borax and/or phenylboronic acid derivatives such as 4-formylphenylboronic acid, one or more soaps or synthetic surfactants, polyols such as glycerine, pH controlling compounds such as fatty acids, citric acid, acetic acid and/or formic acid, and/or a salt of a monovalent cation and an organic anion wherein the monovalent cation may be for example $Na^+$, $K^+$ or $NH_4^+$ and the organic anion may be for example formate, acetate, citrate or lactate such that the salt of a monovalent cation and an organic anion may be, for example, sodium formate.

The laundry soap bar may also contain complexing agents like EDTA and HEDP, perfumes and/or different type of fillers, surfactants e.g. anionic synthetic surfactants, builders, polymeric soil release agents, detergent chelators, stabilizing agents, fillers, dyes, colorants, dye transfer inhibitors, alkoxylated polycarbonates, suds suppressers, structurants, binders, leaching agents, bleaching activators, clay soil removal agents, anti-redeposition agents, polymeric dispersing agents, brighteners, fabric softeners, perfumes and/or other compounds known in the art.

The laundry soap bar may be processed in conventional laundry soap bar making equipment such as but not limited to: mixers, plodders, e.g a two stage vacuum plodder, extruders, cutters, logo-stampers, cooling tunnels and wrappers. The invention is not limited to preparing the laundry soap bars by any single method. The premix of the invention may be added to the soap at different stages of the process. For example, the premix containing a soap, an enzyme, optionally one or more additional enzymes, a protease inhibitor, and a salt of a monovalent cation and an organic anion may be prepared and the mixture is then plodded. The enzyme and optional additional enzymes may be added at the same time as the protease inhibitor for example in liquid form. Besides the mixing step and the plodding step, the process may further comprise the steps of milling, extruding, cutting, stamping, cooling and/or wrapping.

Granular Detergent Formulations

A granular detergent may be formulated as described in WO09/092,699, EP1705241, EP1382668, WO07/001,262, US6472364, WO04/074419 or WO09/102,854. Other useful detergent formulations are described in WO09/124,162, WO09/124,163, WO09/117,340, WO09/117,341, WO09/117,342, WO09/072,069, WO09/063,355, WO09/132,870, WO09/121,757, WO09/112,296, WO09/112,298, WO09/103,822, WO09/087,033, WO09/050,026, WO09/047,125, WO09/047,126, WO09/047,127, WO09/047,128, WO09/021,784, WO09/010,375, WO09/000,605, WO09/122,125, WO09/095,645, WO09/040,544, WO09/040,545, WO09/024,780, WO09/004,295, WO09/004,294, WO09/121,725, WO09/115,391, WO09/115,392, WO09/074,398, WO09/074,403, WO09/068,501, WO09/065,770, WO09/021,813, WO09/030,632, and WO09/015,951.

WO2011025615, WO2011016958, WO2011005803, WO2011005623, WO2011005730, WO2011005844, WO2011005904, WO2011005630, WO2011005830, WO2011005912, WO2011005905, WO2011005910, WO2011005813, WO2010135238, WO2010120863, WO2010108002, WO2010111365, WO2010108000, WO2010107635, WO2010090915, WO2010033976, WO2010033746, WO2010033747, WO2010033897, WO2010033979, WO2010030540, WO2010030541, WO2010030539, WO2010024467, WO2010024469, WO2010024470, WO2010025161, WO2010014395, WO2010044905,

WO2010145887, WO2010142503, WO2010122051, WO2010102861, WO2010099997, WO2010084039, WO2010076292, WO2010069742, WO2010069718, WO2010069957, WO2010057784, WO2010054986, WO2010018043, WO2010003783, WO2010003792,

WO2011023716, WO2010142539, WO2010118959, WO2010115813, WO2010105942, WO2010105961, WO2010105962, WO2010094356, WO2010084203, WO2010078979, WO2010072456, WO2010069905, WO2010076165, WO2010072603, WO2010066486, WO2010066631, WO2010066632, WO2010063689, WO2010060821, WO2010049187, WO2010031607, WO2010000636,

The present invention is further described by the following examples that should not be construed as limiting the scope of the invention.

EXAMPLES

Materials and Methods

Protease Assays
1) Suc-AAPF-pNA Assay:
pNA substrate: Suc-AAPF-pNA (Bachem L-1400).
Temperature: Room temperature (25° C.)
Assay buffers: 100 mM succinic acid, 100 mM HEPES, 100 mM CHES, 100 mM CABS, 1 mM $CaCl_2$, 150 mM KCl, 0.01% Triton X-100 adjusted to pH-values 2.0, 3.0, 4.0, 5.0, 6.0, 7.0, 8.0, 9.0, 10.0, and 11.0 with HCl or NaOH. 20 µl protease (diluted in 0.01% Triton X-100) was mixed with 100 mM assay buffer. The assay was started by adding 100 µl pNA substrate (50 mg dissolved in 1.0 ml DMSO and further diluted 45× with 0.01% Triton X-100). The increase in $OD_{405}$ was monitored as a measure of the protease activity.

2) Protazyme AK Assay:
Substrate: Protazyme AK tablet (cross-linked and dyed casein; from Megazyme)
Temperature: controlled (assay temperature).
Assay buffer: 100 mM succinic acid, 100 mM HEPES, 100 mM CHES, 100 mM CABS, 1 mM $CaCl_2$, 150 mM KCl, 0.01% Triton X-100, pH 6.5 or pH 7.0.

A Protazyme AK tablet was suspended in 2.0 ml 0.01% Triton X-100 by gentle stirring. 500 µl of this suspension and 500 µl assay buffer were dispensed in an Eppendorf tube and placed on ice. 20 µl protease sample (diluted in 0.01% Triton X-100) was added. The assay was initiated by transferring the Eppendorf tube to an Eppendorf thermomixer, which was set to the assay temperature. The tube was incubated for 15 minutes on the Eppendorf thermomixer at its highest shaking rate (1400 rpm.). The incubation was stopped by transferring the tube back to the ice bath. Then the tube was centrifuged in an ice cold centrifuge for a few minutes and 200 µl supernatant was transferred to a microtiter plate. $OD_{650}$ was read as a measure of protease activity. A buffer blind was included in the assay (instead of enzyme).

3) Suc-AAPX-pNA Assay:
pNA substrates:
  Suc-AAPA-pNA (Bachem L-1775)
  Suc-AAPR-pNA (Bachem L-1720)
  Suc-AAPD-pNA (Bachem L-1835)
  Suc-AAPI-pNA (Bachem L-1790)
  Suc-AAPM-pNA (Bachem L-1395)
  Suc-AAPV-pNA (Bachem L-1770)

Suc-AAPL-pNA (Bachem L-1390)
Suc-AAPE-pNA (Bachem L-1710)
Suc-AAPK-pNA (Bachem L-1725)
Suc-AAPF-pNA (Bachem L-1400)
Temperature: Room temperature (25° C.)
Assay buffer: 100 mM succinic acid, 100 mM HEPES, 100 mM CHES, 100 mM CABS, 1 mM $CaCl_2$, 150 mM KCl, 0.01% Triton X-100, pH 9.0.

20 µl protease (diluted in 0.01% Triton X-100) was mixed with 100 µl assay buffer. The assay was started by adding 100 µl pNA substrate (50 mg dissolved in 1.0 ml DMSO and further diluted 45× with 0.01% Triton X-100). The increase in $OD_{405}$ was monitored as a measure of the protease activity.

o-Phthaldialdehyde (OPA) Assay

This assay detects primary amines and hence cleavage of peptide bonds by a protease can be measured as the difference in absorbance between a protease treated sample and a control sample. The assay is conducted essentially according to Nielsen et al. (Nielsen, P M, Petersen, D, Dampmann, C. Improved method for determining food protein degree of hydrolysis, 2001, *J Food Sci*, 66: 642-646).

500 µl of sample is filtered through a 100 kDa Microcon centrifugal filter (60 min, 11,000 rpm, 5° C.). The samples are diluted appropriately (e.g. 10, 50 or 100 times) in deionizer water and 25 µl of each sample is loaded into a 96 well microtiter plate (5 replicates). 200 µl OPA reagent (100 mM di-sodium tetraborate decahydrate, 3.5 mM sodium dodecyl sulphate (SDS), 5.7 mM di-thiothreitol (DDT), 6 mM o-phthaldialdehyde) is dispensed into all wells, the plate is shaken (10 sec, 750 rpm) and absorbance measured at 340 nm.

Soybean-Maize Meal Assay (SMM Assay)

An end-point assay using soybean-maize meal as substrate was used for obtaining the activity profile of the proteases at pH 3-7.

Substrate: Soybean meal-maize meal mixed in a 30:70 ratio.

Assay buffers: 9 buffers containing 100 mM succinic acid, 100 mM HEPES, 100 mM CHES, 100 mM CAPS, 1 mM $CaCl_2$, 150 mM KCl, 0.01% Triton X-100 were prepared and adjusted using HCl or NaOH to a pH value such that after soybean-maize meal substrate (1 g) had been mixed with assay buffer (10 mL) to give a slurry, the final pH of the slurry was one of the following pH's: 3.0, 4.0, 5.0, 6.0, 7.0, 8.0, 9.0, 10.0 and 11.0.

Substrate slurry (2 mL) was mixed for 30 min before protease addition and incubation for 3 hours at 40° C. (500 rpm). Protease (200 mg enzyme protein/kg dry matter) was dissolved in 100 µl 100 mM sodium acetate (NaOAc) buffer (9.565 g/l NaOAc, 1.75 g/l acetic acid, 5 mM $CaCl_2$, 0.01% BSA, 0.01% Tween20, pH 6.0) and added. Supernatants are collected after centrifugation (10 min, 4000 rpm, 0° C.) and protein activity was determined using a colorimetric assay based on the o-phthat-dialdehyde (OPA) method essentially according to Nielsen et al. (Nielsen, P M, Petersen, D, Dampmann, C. Improved method for determining food protein degree of hydrolysis. J Food Sci, 2001, 66: 642-646). This assay detects free α-amino groups and hence protease activity can be measured as an increase in absorbance. First 500 µl of each supernatant is filtered through a 100 kDa Microcon filter by centrifugation (60 min, 11,000 rpm, 5° C.). The samples are diluted 10× in deionized water and 25 µl of each sample is loaded into a 96 well microtiter plate (5 replicates). Finally 200 µl OPA reagent is dispensed into all wells and the plate is shaken (10 sec, 750 rpm) and absorbance measured at 340 nm. The level of protease activity is calculated as the difference between absorbance in the enzyme treated sample and the blank sample and expressed as 'OD x dilution factor'.

Results are provided in Example 4 below

Strains

The nucleotide sequence encoding the S1 protease 1 from *Saccharopolyspora erythraea* was published by Oliynyk et al in 'Complete genome sequence of the erythromycin-producing bacterium *Saccharopolyspora erythraea* NRRL23338', 2007, Nat. Biotechnol. 25:447-453 and the gene was submitted to EMBL/GenBank under accession number EMBL: AM420293. According to Oliynyk, 'the strain used, NRRL23338, is the original form of the type strain of *S. erythraca* NRRL2338, which is now listed as NRRL23338 white in the NRRL database'. The NRRL database indicates (under NRRL number B-24071 which corresponds to NRRL 23338 white) that the 'white colony variant was isolated from growth from ampule from second lyophilization'. The reference for NRRL2338 refers to U.S. Pat. No. 2,653,899 wherein it is stated that the original sample of *S. erythraca* NRRL2338 was obtained as a soil sample from Ilonio City, Phillipine Islands on or before 1952.

Example 1

Construction of a *Bacillus subtilis* Strain for the Expression of the S1 Protease 1 from *Saccharopolyspora erythraea*

Based on the published nucleotide sequence identified as SEQ ID NO: 1, a synthetic gene having SEQ ID NO: 3 was synthesized by Gene Art (GENEART AG BioPark, Josef-Engert-Str. 11, 93053, Regensburg, Germany). The synthetic gene was subcloned using ClaI and MluI restriction sites into a *Bacillus* expression vector as described in Example 1 of PCT/EP11/064,585. Transformants were selected on LB plates supplemented with 6 µg of chloramphenicol per ml.

The recombinant *Bacillus subtilis* clone containing the integrated expression construct was selected and designated *Saccharopolyspora erythraea* S1-1. It was cultivated on a rotary shaking table in 500 mL baffled Erlenmeyer flasks each containing 100 ml casein-based media supplemented with 34 mg/l chloramphenicol. The clone was cultivated for 3 days at 37° C. The enzyme containing supernatants were harvested and the enzyme purified as described in Example 2. The purified peptidase was designated S1 protease 1 from *Saccharopolyspora erythraea*.

Example 2

Purification of the S1 Protease 1 from *Saccharopolyspora erythraea* from Strain *Saccharopolyspora erythraea* S1-1

The *Saccharopolyspora erythraea* S1-1 broth was centrifuged (20000×g, 20 min) and the supernatant was carefully decanted from the precipitate. The supernatant was filtered through a Nalgene 0.2 µm filtration unit in order to remove the rest of the *Bacillus* host cells. Solid ammonium sulphate was added to the 0.2 µm filtrate to a final ammonium sulphate concentration of 1.4M $(NH_4)_2SO_4$. The ammonium sulphate adjusted 0.2 µm filtrate was applied to a Phenyl Toyopearl 650S column (from TosoHaas) equilibrated in 100 mM $H_3BO_3$, 10 mM MES/NaOH, 2 mM $CaCl_2$, 1.4M $(NH_4)_2SO_4$, pH 6.0. After washing the column extensively with the equilibration buffer, the protease was eluted with a linear $(NH_4)_2SO_4$ gradient (1.4->0M) in the same buffer over three column volumes. Fractions from the column were analysed for protease activity (using the Suc-AAPF-pNA assay at pH 9). The protease peak was pooled and transferred to 100 mM $H_3BO_3$, 10 mM MES/NaOH, 2 mM $CaCl_2$, pH 6.0 on a G25 Sephadex column (from GE Healthcare). The G25 sephadex transferred enzyme was slightly turbid and was filtered through a Nalgene 0.2 μm filtration unit. The pH of the filtered enzyme solution was adjusted to pH 4.5 with 20% $CH_3COOH$ and the solution was applied to a SP-sepharose FF column (from GE Healthcare) equilibrated in 20 mM $CH_3COOH$/NaOH, 1 mM $CaCl_2$, pH 4.5. After washing the column extensively with the equilibration buffer, the protease was eluted with a linear NaCl gradient (0-->0.5M) in the same buffer over five column volumes. Fractions from the column were analysed for protease activity (using the Suc-AAPF-pNA assay at pH 9). The protease peak was pooled and transferred to 10 mM Succinic acid/NaOH, pH 3.5 on a G25 Sephadex column (from GE Healthcare). The G25 sephadex transferred enzyme was applied to a SOURCE S column (from GE Healthcare) equilibrated in 10 mM Succinic acid/NaOH, pH 3.5. After washing the column extensively with the equilibration buffer, the protease was eluted with a linear NaCl gradient (0-->0.5M) in the same buffer over thirty column volumes. Fractions from the column were analysed for protease activity (using the Suc-AAPF-pNA assay at pH 9) and active fractions were further analysed by SDS-PAGE. Fractions, where only one band was seen on the coomassie stained SDS-PAGE gel, were pooled and the pH was adjusted to pH 5.0 with 3% NaOH. The adjusted pool from the SOURCE S column was the purified preparation and was used for further characterization.

Example 3

Characterization of the S1 Protease 1 from *Saccharopolyspora erythraea*

The Suc-AAPF-pNA assay was used for obtaining the pH-activity profile and the pH-stability profile (residual activity after 2 hours at indicated pH-values). For the pH-stability profile the protease was diluted 10× in the different assay buffers to reach the pH-values of these buffers and then incubated for 2 hours at 37° C. After incubation, the pH of the protease incubations was transferred to the same pH-value, before assay for residual activity, by dilution in the pH 10.0 Assay buffer. The Protazyme AK assay was used for obtaining the temperature-activity profile at pH 7.0. The Suc-AAPX-pNA assay and ten different Suc-AAPX-pNA substrates were used for obtaining the P1-specificity of the enzymes at pH 9.0.

The results are shown in Tables 2-5 below. For Table 2, the activities are relative to the optimal pH for the enzyme. For Table 3, the activities are residual activities relative to a sample, which was kept at stable conditions (5° C., pH 9.0). For Table 4, the activities are relative to the optimal temperature at pH 7.0 for the enzyme. For Table 5, the activities are relative to the best substrate (Suc-AAPF-pNA) for the enzyme.

TABLE 2 pH-activity profile at 25° C.

| pH | S1 Protease 1 from *Saccharopolyspora erythraea* | Protease 10R |
|---|---|---|
| 2 | 0.00 | |
| 3 | 0.00 | 0.00 |
| 4 | 0.02 | 0.02 |
| 5 | 0.09 | 0.07 |
| 6 | 0.26 | 0.21 |
| 7 | 0.45 | 0.44 |
| 8 | 0.74 | 0.67 |
| 9 | 0.96 | 0.88 |
| 10 | 1.00 | 1.00 |
| 11 | 1.00 | 0.93 |

TABLE 3 pH-stability profile (residual activity after 2 hours at 37° C.)

| pH | S1 Protease 1 from *Saccharopolyspora erythraea* | Protease 10R |
|---|---|---|
| 2 | 0.98 | 0.78 |
| 3 | 0.99 | 1.03 |
| 4 | 0.99 | 0.99 |
| 5 | 1.02 | 1.00 |
| 6 | 0.96 | 1.03 |
| 7 | 1.00 | 1.01 |
| 8 | 0.99 | 0.98 |
| 9 | 0.99 | 0.99 |
| 10 | 0.96 | 0.99 |
| 11 | 0.95 | 0.86 |
| After 2 hours at 5° C. | 1.00 (at pH 9) | 1.00 (at pH 9) |

TABLE 4

Temperature activity profile at pH 7.0 or pH 6.5

| Temp (° C.) | S1 Protease 1 from *Saccharopolyspora erythraea* (pH 7) | Protease 10R (pH 6.5) |
|---|---|---|
| 15 | 0.01 | 0.01 |
| 25 | 0.01 | 0.02 |
| 37 | 0.04 | 0.06 |
| 50 | 0.10 | 0.13 |
| 60 | 0.19 | 0.35 |
| 70 | 0.59 | 0.96 |
| 80 | 1.00 | 1.00 |
| 90 | 0.16 | 0.18 |

TABLE 5

P1-specificity on 10 Suc-AAPX-pNA substrates at pH 9.0

| Suc-AAPX-pNA | S1 Protease 1 from *Saccharopolyspora erythraea* | Protease 10R |
|---|---|---|
| Suc-AAPA-pNA | 0.03 | 0.13 |
| Suc-AAPR-pNA | 0.08 | 0.09 |
| Suc-AAPD-pNA | 0.00 | 0.00 |
| Suc-AAPI-pNA | 0.00 | 0.00 |
| Suc-AAPM-pNA | 0.40 | 0.78 |
| Suc-AAPV-pNA | 0.01 | 0.01 |
| Suc-AAPL-pNA | 0.19 | 0.18 |
| Suc-AAPE-pNA | 0.00 | 0.00 |
| Suc-AAPK-pNA | 0.04 | 0.08 |
| Suc-AAPF-pNA | 1.00 | 1.00 |

The pH-activity on the Suc-AAPF-pNA substrate, the pH-stability profile (residual activity after 2 hours at 37° C.), the temperature activity profile on Protazyme AK at pH 7.0 and the P1-specificity on 10 Suc-AAPF-pNA substrates at pH 9.0 for the S1 protease 1 from *Saccharomonospora erythraea* compared with the data for Protease 10R are also shown in FIG. 1 to FIG. 4.

Other Characteristics for the S1 Protease 1 from *Saccharopolyspora erythraea*
Inhibitor: PMSF.
Determination of the N-terminal sequence was: YNWGGD.
The relative molecular weight as determined by SDS-PAGE was approx. $M_r$=20 kDa.
The molecular weight determined by intact molecular weight analysis was 19337.5 Da.
The mature sequence from MS-EDMAN data (and as deduced from SEQ ID NO: 1 and SEQ ID NO: 3):

```
                                         (SEQ ID NO: 5)
YNVVGGDAYYMGGRCSVGFSVRSSSGQAGFVTAGHCGTRGTAVSGY

NQVAMGSFQGSSFPNNDYAWVSVNSNWTPQPWVNLYNGSARVVSGS

SAAPVGSSICRSGSTTGWHCGSVQALNQTVRYAEGTVYGLTRTNVC

AEPGDSGGSFISGNQAQGMTSGGSGNCSSGGTTYFQPVNEALSAYG

LSLVRG.
```

The calculated molecular weight from this mature sequence was 19336.9 Da.

Example 4

Protease Activity in Soybean-Maize Meal Assay (SMM Assay)

Figure 5:
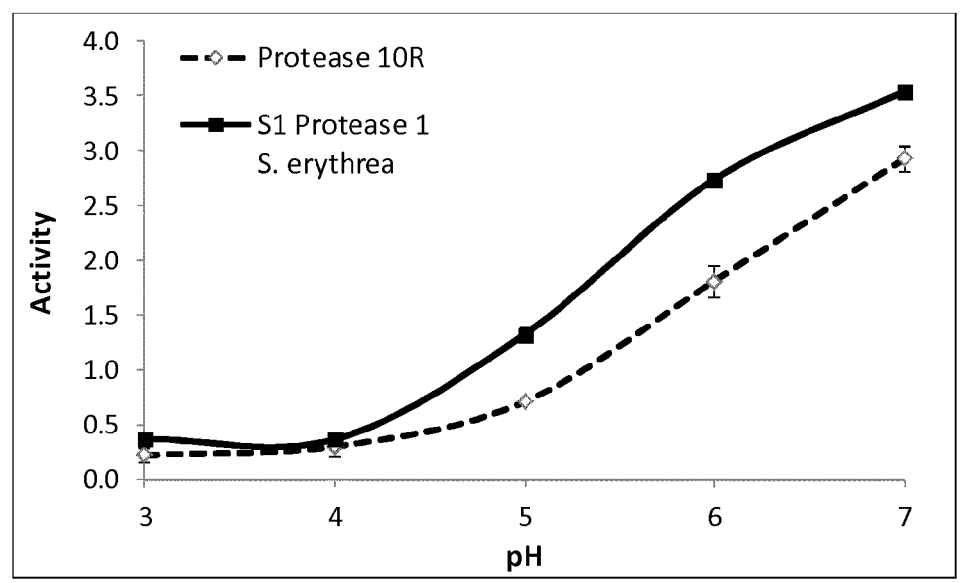
FIG. 5 shows the pH activity on soybean-maize meal at pH 3.0, 4.0, 5.0, 6.0 and 7.0 (40° C.) for the S1 Protease 1 from *Saccharomonospora erythraea* compared to the 10R protease.

A soybean-maize meal assay was used to describe the activity of the proteases on a substrate relevant for animal feed. The results are shown in Table 6 below and in FIG. 5. The proteolytic activity of the S1 protease 1 from *Saccharopolyspora erythraea* on soybean-maize meal increases with increasing pH from pH 3 to pH 7, and the activity in the entire pH range is higher than for protease 10R indicating that the S1 protease 1 from *Saccharopolyspora erythraea* could be more efficient at protein hydrolysis in the gastro-intestinal tract of e.g. pigs and poultry.

TABLE 6

Protease activity on soybean-maize meal at pH 3.0, 4.0, 5.0, 6.0 and 7.0

| | S1 Protease 1 from *Saccharopolyspora erythraea* | | Protease 10R | |
|---|---|---|---|---|
| pH | Average | Standard deviation | Average | Standard deviation |
| 3.0 | 0.37 | 0.01 | 0.22 | 0.06 |
| 4.0 | 0.36 | 0.03 | 0.30 | 0.10 |
| 5.0 | 1.32 | 0.07 | 0.71 | 0.01 |
| 6.0 | 2.74 | 0.06 | 1.81 | 0.14 |
| 7.0 | 3.54 | 0.06 | 2.92 | 0.11 |

Example 5

Proteolytic Activity on Crop, Gizzard and Ileum Digesta from Broiler Chickens

Crop, gizzard and ileum digesta material from 21 day old broiler chickens fed a corn-soy diet was collected; freeze dried and ground using a small coffee mill. The ground samples were suspended (47% w/v) in the following buffers and left to hydrate at 4° C. over night (no stirring):

Crop buffer: 100 mM HEPES, 1 mM $CaCl_2$.2 $H_2O$, 150 mM KCl, 0.01% Triton X-100, adjusted to pH 5 using HCl Gizzard buffer: 100 mM succinic acid, 1 mM $CaCl_2$.2 $H_2O$, 150 mM KCl, 0.01% Triton X-100, adjusted to pH 1.67 using HCl Ileum buffer: 100 mM HEPES, 1 mM $CaCl_2$.2 $H_2O$, 150 mM KCl, 0.01% Triton X-100, adjusted to pH 7.2 using HCl The resulting pH was: pH 5 in crop samples; pH 3 in gizzard samples; and pH 7 in ileum samples. The suspensions were heated to 40° C. and 1 ml was dispensed into tubes kept at 40° C. Three tubes representing blank ($T_0$) were immediately centrifuged (3000×g, 0° C., 10 min) and the supernatants frozen. Either enzyme (200 mg enzyme protein/kg substrate) in 50 μL 100 mM sodium acetate buffer (9.565 g/l NaOAc, 1.75 g/l acetic acid, 5 mM CaCl2, 0.01% BSA, 0.01% Tween20, pH 6.0) or just sodium acetate buffer (50 μL) for the blank samples was added to the tubes and crop and ileum samples were incubated for 3 hours ($T_3$) while the gizzard samples were incubated for 1 hour ($T_1$) at 40° C. while shaking (500 rpm). The samples were centrifuged (3000×g, 0° C., 10 min) and supernatants recovered and frozen. The proteolytic activity was determined by analyzing primary amines using the o-phthaldialdehyde (OPA) assay.

The results are shown in Table 7. For each of the digesta types (crop, gizzard and ileum) there was a significant difference between the level of soluble primary amines in the blank $T_0$ sample and the blank samples incubated for 1 or 3 hours. This difference may be ascribed to solubilisation and activity of proteases present in the substrate and originating from either the diet raw materials or the animal. The S1 protease 1 from *Saccharopolyspora erythraea* significantly increased the level of soluble primary amines in crop and ileum samples compared to the blank sample. The increase observed by the S1 protease 1 from *Saccharopolyspora erythraea* was as high as or numerically higher than that of Protease 10R, indicating a slightly higher proteolytic potential for this protease on the given substrate.

TABLE 7

Proteolytic activity of the S1 Protease 1 from *Saccharopolyspora erythraea* compared to Protease 10R when incubated with broiler digesta and expressed as level of primary amines measured by the OPA assay ($OD_{340}$ × dilution factor)

| Treatment | Crop (3 hours) | Gizzard (1 hour) | Ileum (3 hours) |
|---|---|---|---|
| Blank ($T_0$) | 2.21 ± 0.02 [c] | 2.95 ± 0.02 [b] | 9.37 ± 0.08 [b] |
| Blank | 3.54 ± 0.02 [b] | 3.85 ± 0.13 [a] | 14.42 ± 0.52 [a] |
| Protease 10R | 3.85 ± 0.07 [a] | 3.87 ± 0.13 [a] | 14.74 ± 0.16 [a] |
| S1 Protease 1 from *Saccharopolyspora erythraea* | 3.87 ± 0.10 [a] | 3.89 ± 0.04 [a] | 14.84 ± 0.14 [a] |

[a, b, c, d] Values within a column that are not connected by the same superscript letters are statistically different as determined by the Tukey Kramer test ($\alpha$ = 0.05) provided by the ANOVA procedure (SAS Institute Inc.).

Example 6

Thermostability

An aliquot of the protein sample of protease (purified as described in Example 2) is either desalted or buffer-changed into 20 mM Na-acetate, pH 4.0 using a prepacked PD-10 column or dialysed against 2×500 ml 20 mM Na-acetate, pH 4.0 at 4° C. in a 2-3 h step followed by an overnight step. The sample is 0.45 μm filtered and diluted with buffer to approx. 2 A280 units. The dialysis buffer is used as reference in Differential Scanning calorimetry (DSC). The samples are degassed using vacuum suction and stirring for approx. 10 minutes.

A DSC scan is performed on a MicroCal VP-DSC at a constant scan rate of 1.5° C./min from 20-90° C. Data-handling is performed using the MicroCal Origin software (version 4.10), and the denaturation temperature, $T_d$ (also called the melting temperature, $T_m$) is defined as the temperature at the apex of the peak in the thermogram.

Example 7

Steam Stability

Residual activity of the protease after steam treatment may be evaluated using the following assay.

In these experiments a modified set-up is used whereby the steam is provided from a steam generator and led into the box. The samples placed on a plate are inserted into the box through a drawer when the temperature has reached ca. 93-94° C. Upon the insertion of the samples the temperature drops 4° C. Incubation is performed for 30 seconds while the temperature remains approximately constant at 90° C. Thereafter the plate is quickly removed from the box, the samples placed on ice, re-suspended and evaluated with respect to protease activity using the Suc-AAPF-pNA or o-Phthaldialdehyde (OPA) assay. Each enzyme sample is compared to a similar sample that had not been steam treated in order to calculate residual activity.

Example 8

Pelleting Stability Tests

The enzyme granulation is performed in a manner as described in U.S. Pat. No. 4,106,991, Example 1. The obtained granulate is dried in a fluid bed to a water content below 1% and sifted to obtain a product with the particle range 250 μm to 850 μm. Finally, the product is coated with palm oil and calcium carbonate in a manner as described in U.S. Pat. No. 4,106,991, Example 22.

Approximately 50 g enzyme granulate is pre-mixed with 10 kg feed for 10 minutes in a small horizontal mixer. This premix is mixed with 90 kg feed for 10 minutes in a larger horizontal mixer. From the mixer the feed is led to the conditioner (a cascade mixer with steam injection) at a rate of approximately 300 kg/hour. The conditioner heats up the feed to 95° C. (measured at the outlet) by injecting steam. The residence time in the conditioner is 30 seconds. From the conditioner the feed is led to a Simon Heesen press equipped with 3.0×35 mm horizontal die and pressed to pellets with a length of around 15 mm. After the press the pellets are placed in an air cooler and cooled for 15 minutes.

The protease activity is measured using the Suc-AAPF-pNA assay prior to pelleting and in the feed pellets after pelleting. Pelleting stability is determined by comparing the protease activity in pelleted feed relative to the activity in non-pelleted feed.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

---

What is claimed is:

1. A method for improving the nutritional value of or increasing digestible and/or soluble protein in an animal feed, comprising adding a polypeptide having protease activity to the feed, wherein the amino acid sequence of the polypeptide is at least 90% identical to SEQ ID NO: 5.

2. The method of claim 1, wherein the amino acid sequence of the polypeptide is at least 95% identical to SEQ ID NO: 5.

3. The method of claim 1, wherein the amino acid sequence of the polypeptide is at least 97% identical to SEQ ID NO: 5.

4. The method of claim 1, wherein the amino acid sequence of the polypeptide is at least 98% identical to SEQ ID NO: 5.

5. The method of claim 1, wherein the amino acid sequence of the polypeptide is at least 99% identical to SEQ ID NO: 5.

6. The method of claim 1, wherein the amino acid sequence of the polypeptide is SEQ ID NO: 5.

7. A method of feeding an animal, comprising feeding an animal with an animal feed comprising a polypeptide having protease activity, wherein the amino acid sequence of the polypeptide is at least 90% identical to SEQ ID NO: 5.

8. The method of claim 7, wherein the amino acid sequence of the polypeptide is at least 95% identical to SEQ ID NO: 5.

9. The method of claim 7, wherein the amino acid sequence of the polypeptide is at least 97% identical to SEQ ID NO: 5.

10. The method of claim 7, wherein the amino acid sequence of the polypeptide is at least 98% identical to SEQ ID NO: 5.

11. The method of claim 7, wherein the amino acid sequence of the polypeptide is at least 99% identical to SEQ ID NO: 5.

12. The method of claim 7, wherein the amino acid sequence of the polypeptide is SEQ ID NO: 5.

13. The method of claim 7, wherein the animal feed comprises at least one fat-soluble vitamin, and/or at least one water-soluble vitamin, and/or at least one trace mineral.

14. The method of claim 7, wherein the animal feed further comprises one or more amylases; galactanases; alpha-galactosidases; proteases, phospholipases, phytases; beta-glucanases, xylanases; or any mixture thereof.

* * * * *